United States Patent
Zhu et al.

(10) Patent No.: US 6,218,382 B1
(45) Date of Patent: Apr. 17, 2001

(54) SELECTIVE FACTOR XA INHIBITORS

(75) Inventors: Bing-Yan Zhu; Robert Scarborough, both of Belmont, CA (US)

(73) Assignee: COR Therapeutics, INC, South San Francisco, CA (US)

( * ) Notice: Subject to any disclaimer, the term of this patent is extended or adjusted under 35 U.S.C. 154(b) by 0 days.

(21) Appl. No.: 09/132,258

(22) Filed: Aug. 11, 1998

Related U.S. Application Data

(60) Provisional application No. 60/084,185, filed on Aug. 11, 1997.

(51) Int. Cl.[7] .................. A61K 31/55; A61P 7/02; C07D 487/00; C07D 491/00; C07D 498/00
(52) U.S. Cl. .................. 514/212.07; 540/523
(58) Field of Search ............ 540/523; 514/212.07

(56) References Cited

U.S. PATENT DOCUMENTS

| | | | |
|---|---|---|---|
| 3,352,866 | 11/1967 | Dornfeld | 260/268 |
| 3,845,046 | 10/1974 | Fauran et al. | 260/247.8 |
| 4,178,438 | 12/1979 | Haase et al. | 536/30 |
| 4,251,438 | 2/1981 | Moon | 260/112.5 R |
| 4,341,698 | 7/1982 | Carr et al. | 260/112.5 R |
| 4,588,587 | 5/1986 | Gasic | 424/95 |
| 4,720,493 | 1/1988 | Kawakita et al. | 514/230 |
| 5,028,610 | 7/1991 | Hirai et al. | 514/259 |
| 5,120,718 | 6/1992 | Goldman et al. | 514/32 |
| 5,164,371 | 11/1992 | Edwards et al. | 514/18 |
| 5,164,388 | 11/1992 | De et al. | 514/235.8 |
| 5,194,614 | 3/1993 | Andrieux et al. | 544/200 |
| 5,276,051 | 1/1994 | Lesieur et al. | 514/415 |
| 5,281,585 | 1/1994 | Duggan et al. | 514/79 |
| 5,294,713 | 3/1994 | Sugihara et al. | 544/384 |
| 5,443,815 | 8/1995 | Dean et al. | 514/415 |
| 5,492,895 | 2/1996 | Vlasuk et al. | 514/18 |
| 5,521,179 | 5/1996 | Bernstein et al. | 514/415 |
| 5,523,308 | 6/1996 | Costanzo et al. | 514/317 |
| 5,563,136 | 10/1996 | Capet et al. | 514/221 |
| 5,583,146 | 12/1996 | Kimball et al. | 514/326 |
| 5,612,363 | 3/1997 | Mohan et al. | 514/392 |
| 5,618,811 | 4/1997 | Lowe, III | 514/218 |
| 5,632,898 | 5/1997 | Jung et al. | 210/656 |
| 5,668,289 | 9/1997 | Sanderson et al. | 546/293 |
| 5,703,208 | 12/1997 | Semple et al. | 530/331 |
| 5,714,499 | 2/1998 | Semple et al. | 514/316 |
| 5,721,214 | 2/1998 | Marlowe et al. | 514/18 |
| 5,776,902 | 7/1998 | Bachovchin | 514/18 |
| 5,861,509 | 1/1999 | Schnorrenberg et al. | 544/130 |
| 5,948,785 | 9/1999 | Akahoshi et al. | 514/269 |

FOREIGN PATENT DOCUMENTS

| | | |
|---|---|---|
| 2 071 744 | 12/1992 | (CA) . |
| 2 126 026 | 12/1994 | (CA) . |
| 0 167 919 | 1/1986 | (EP) . |
| 0 239 461 | 9/1987 | (EP) . |
| 0 352 903 | 1/1990 | (EP) . |
| 0 365 992 | 5/1990 | (EP) . |
| 0 471 651 | 2/1992 | (EP) . |
| 0 512 831 | 11/1992 | (EP) . |
| 0 529 858 | 3/1993 | (EP) . |
| 0 688 788 | 12/1995 | (EP) . |
| 0 761 220 | 3/1997 | (EP) . |
| 0 765 873 | 4/1997 | (EP) . |
| 2 287 027 | 9/1995 | (GB) . |
| 53-34735 | 3/1978 | (JP) . |
| 58-96075 | 6/1983 | (JP) . |
| 58-194873 | 11/1983 | (JP) . |
| 58-216170 | 12/1983 | (JP) . |
| 2-83375 | 3/1990 | (JP) . |
| 3-148223 | 6/1991 | (JP) . |
| 5-241287 | 9/1993 | (JP) . |
| 6 327 488 | 11/1994 | (JP) . |
| 93/09133 | 5/1993 | (WO) . |
| 93/15756 | 8/1993 | (WO) . |
| 93/21213 | 10/1993 | (WO) . |
| 94/08941 | 4/1994 | (WO) . |
| 94/13693 | 6/1994 | (WO) . |
| WO 94/13648 | 6/1994 | (WO) . |
| 94/17817 | 8/1994 | (WO) . |
| 94/21673 | 9/1994 | (WO) . |
| 94/25051 | 11/1994 | (WO) . |
| 95/06038 | 3/1995 | (WO) . |
| 95/28420 | 10/1995 | (WO) . |
| WO 95/28399 | 10/1995 | (WO) . |
| 95/29189 | 11/1995 | (WO) . |
| 95/35308 | 12/1995 | (WO) . |
| 95/35311 | 12/1995 | (WO) . |
| 95/35312 | 12/1995 | (WO) . |
| 95/35313 | 12/1995 | (WO) . |
| 96/01338 | 1/1996 | (WO) . |
| 96/18644 | 6/1996 | (WO) . |
| 96/19483 | 6/1996 | (WO) . |
| 96/19491 | 6/1996 | (WO) . |
| 96/19493 | 6/1996 | (WO) . |
| 96/24609 | 8/1996 | (WO) . |
| 96/31214 | 10/1996 | (WO) . |
| 96/31504 | 10/1996 | (WO) . |
| 96/32110 | 10/1996 | (WO) . |
| 96/40653 | 12/1996 | (WO) . |
| 96/40744 | 12/1996 | (WO) . |
| 97/01338 | 1/1997 | (WO) . |
| 97/05160 | 2/1997 | (WO) . |
| 97/14417 | 4/1997 | (WO) . |
| 97/17363 | 5/1997 | (WO) . |
| 97/30073 | 8/1997 | (WO) . |
| 98/09987 | 3/1998 | (WO) . |
| 98/16523 | 4/1998 | (WO) . |
| 98/16547 | 4/1998 | (WO) . |
| 99/07731 | 2/1999 | (WO) . |
| 99/07732 | 2/1999 | (WO) . |

OTHER PUBLICATIONS

Kaiser et al., Factor Xa Inhibitors as Novel Antithrombotic Agents: Facts and Perspectives, *Cardiovascular Drug Reviews*, 12(3):225–236 (1994).

(List continued on next page.)

*Primary Examiner*—Bruck Kifle
(74) *Attorney, Agent, or Firm*—Morgan, Lewis & Bockius LLP

(57) ABSTRACT

Novel compounds, their salts and compositions related thereto having activity against mammalian factor Xa are disclosed. The compounds are usefull in vitro or in vivo for preventing or treating coagulation disorders.

45 Claims, No Drawings

OTHER PUBLICATIONS

Robl, et al., Dual Metalloprotease Inhibitors. II. Effect of Substitution and Stereochemistry on Benzazepinone Based Mercaptoacetyls, *Bioorganic and Medicinal Chemistry Letters* 4(15):1795–1800 (1994).

Robl, et al., Dual Metalloprotease Inhibitors. 6. Incorporation of Bicyclic and Substituted Monocyclic Azepinones as Dipeptide Surrogates in Angiotensin–Converting Enzyme/Neutral Endopeptidase Inhibitors, *Journal of Medicinal Chemistry,* 39(2):494–502 (1996).

Skiles, et al., *Bioorganic & Medicinal Chemistry Letters,* 3(4):773–778 (1993).

Skiles, et al., Chemical Abstracts, vol. 120, No. 11, (1994) (CA: 120:1350101a).

Stilz, et al., Discovery of an Orally Active Non–Peptide Fibrinogen Receptor Antagonist, *J. Med. Chem.* 39(11):2118–2122 (1996).

Tomatis, et al., Synthesis and pharmacological activity of Leu–Enkephalins modified at $Gly^2$–$Gly^3$ nitrogens, *European Journal of Medicinal Chemistry—Chimica Therapeutica* 16(3):229–232 (1981).

Gennaro, Ed., "Remington's Pharmaceutical Sciences", Mack Publishing Company (1985).

Tourwé, et al., "Conformational Restriction of Tyr and Phe Side Chains in Opioid Peptides: Information About Preferred and Bioactive Side–Chain Topology", Biopolymers, 38:1–12 (1996).

Almquist, et al., "Synthesis and Biological Activity of a Ketomethylene Analogue of a Tripeptide Inhibitor of Angiotensin Converting Enzyme", *J. Med.Chem.* 23:1392–1398 (1980).

Blankenship, et al., "Amino Acid Sequence of Ghilanten: Anticoagulant–Antimetastatic Principle of the South American Leech, *Haementeria ghilianii*", *Biochem, BioPhys. Res. Commun.* 166:1384–1389 (1990).

Bodanszky, "The Principles of Peptide Synthesis", Hafner, et al., Eds., Springer–Verlag, Berlin (1984).

Brankamp, et al., "Ghilantens: Anticoagulants Antimetastatic Proteins from the South American Leech, *Haementeria ghilianii*", *J. Lab. Clin. Med.* 115:89–97 (1990).

Bundgard, "Design of Pro–drugs", pp. 7–9, Elsevier, Amsterdam, 1985.

Bundgard, "Design of Pro–drugs", pp. 21–24, Elsevier, Amsterdam, 1985.

Szelke, et al., CA:97:39405 (1982).

Cappello, et al., "Ancylostoma Factor Xa Inhibitor: Partial Purification and its Identification as a Major Hookworm–derived Anticoagulant in Vitro", *J. Infect. Dis.* 167:1474–1477 (1993).

Claeson, "Synthetic Peptides and Peptidomimetics as Substrates and Inhibitors of Thrombin and Other Proteases in the Blood Coagulation System", *Blood Coag. Fibrinol.* 5:411–436 (1994).

Condra, et al., "Isolation and Structural Characterization of a Potent Inhibitor of Coagulation Factor Xa from the Leech *Haementeria ghilianii*" *Thromb. Haemost.* 61:437–441 (1989).

Cox, "Coagulation Factor X Inhibitor from the Hundred–pace Snake (*Deinagkistrodon Acutus*) Venom", *Toxicon* 31:1445–1457 (1993).

Davie, et al., "The Coagulation Cascade: Initiation, Maintenance and Regulation", *Biochemistry 30:10363–10370* (1991).

Diana, et al., "Picornavirus Inhibitors: Trifluoromethyl Substitution Provides a Global Protective Effect against Hepatic Metabolism", *J. Med. Chem.* 38:1355–1371 (1995).

Diana, et al., "Oxadizaoles as Ester Bioisosteric Replacements in Compounds Related to Disoxaril. Antirhinovirus Activity", *J. Med. Chem.* 37:2421–2436 (1994).

DiMaio, et al., "Synthesis of Chiral Piperazin–2–ones as Model Peptidomimetics", *J. Chem. Soc. Perkins. Trans. I,* 1687–1689 (1989).

Edwards, et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.* 114:1854–1863 (1992).

Edwards, et al., "Peptidyl α–Ketoheterocyclic Inhibitors of Human Neutrophil Elastase. 2. Effect of Varying the Heterocyclic Ring on in Vitro Potency", *J. Med. Chem.* 38:76–85 (1995).

Girard, et al., "Functional Significance of the Kunitz–type Inhibitory Domains of Lipoprotein–associated Coagulation Inhibitor", *Nature* 338:518–520 (1989).

Gross, et al., Eds., "The Peptides: Analysis, Synthesis, Biology", Academic Press, vol. 3 (1981).

Udenfriend, et al., Eds., "The Peptides: Analysis, Synthesis, Biology", Academic Press, vol. 9 (1987).

Hann, *J. Chem. Soc. Perkins. Trans. I,* pp. 307–314 (1982).

Hauptmann, et al., "Comparison of the Anticoagulant and Antithrombotic Effects of Synthetic Thrombin and Factor Xa Inhibitors", *Thromb. Haemost.* 63:220–223 (1990).

Hitomi, et al., "Inhibitory Effect of New Synthetic Protease Inhibitor (FUT–175) on the Coagulation System", *Haemostatsis* 15:164–168 (1985).

Hollenbach, et al., "A Comparative Study of Prothrombinase and Thrombin Inhibitors in a Novel Rabbit Model of Non-Occlusive Deep Vein Thrombosis", *Thromb. Haemost.* 71:357–362 (1994).

Holladay, et al., "Synthesis of Hydroxyethylene and Ketomethylene Dipeptide Isosteres", *Tetrahedron Lett.* 24:4401–4404 (1983).

Hruby, "Conformational Restrictions of Biologically Active Peptides via Amino Acid Side Chain Groups", *Life Sci.* 31:189–199 (1982).

Hudson, et al., "Methionine Enkephalin and Isosteric Analogues", *Int. J. Pept. Prot. Res.* 14:177–185 (1979).

Jacobs, et al., "Isolation and Characterization of a Coagulation Factor Xa Inhibitor from Black Fly Salivary Glands", *Thromb. Haemost.* 64:235–238 (1990).

Jennings–White, et al., "Synthesis of Ketomethylene Analogs of Dipeptides", *Tetrahedron Lett.* 23:2533–2534 (1982).

Kam, et al., "Mechanism–based Isocoumarin Inhibitors for Trypsin and Blood Coagulation Serine Proteases: New Anticoagulants", *Biochemistry* 27:2547–2557 (1988).

Kojima, et al., "Preparations, Solution Conformations and Molecular Structures of N, N'–Ethylene–bridged Dipeptides and their Derivatives", *Int. J. Peptide Protein Res.* 37:468–475 (1991).

Mann, et al., "Surface–Dependent Reactions of the Vitamin K–Dependent Enzyme Complexes", *Blood,* 76:1–16 (1990).

Morley, "Modulation of the Action of Regulatory Peptides by Structural Modification", (General Review) *Trends Pharm. Sci.* pp. 463–468 (1980).

Nagahara, et al., "Dibasic (Amidinoaryl)propanoic Acid Derivatives as Novel Blood Coagulation Factor Xa Inhibitors", *J. Med. Chem.* 37:1200–1207 (1994).

Nutt, et al., "The Amino Acid Sequence of Antistasin: A Potent Inhibitor of Factor Xa Reveals a Repeated Internal Structure", *J. Biol. Chem.* 263:10162–10167 (1988).

Seymour, et al., "Ecotin Is a Potent Anticoagulant and Reversible Tight–binding Inhibitor of Factor Xa", *Biochemistry* 33:3949–3958 (1994).

Silverman, "The Organic Chemistry of Drug Design and Drug Action", pp. 352–401, Academic Press, San Diego, CA. (1992).

Sinha, et al., "Effect of Gamma Carboxylation on Prothrombinase Inhibitory Activity of Catalytically Inactive Factor Xa", *Thromb. Res.* 75:427–436 (1994).

Spatola, et al., "Structure–Activity Relationship of Enkephalins Containing Serially Replaced Thiomethylene Amide Bond Surrogates", *Life Sci.* 38:1243–1249 (1986).

Spatola, "Chemistry and Biochemistry of Amino Acids, Peptides and Proteins", (General Review), B. Weinstein, Eds., Marcell Decker, New York, p. 260. (1983).

Sturzebecher, et al., "Synthetic Inhibitors of Bovine Factor Xa and Thrombin. Comparison of Their Anticoagulant Efficiency", *Thromb. Res.* 54:245–252 (1989).

Tidwell, et al., "Strategies for Anticoagulation with Synthetic Protease Inhibitors. Xa Inhibitors Versus Thrombin Inhibitors", *Thromb. Res.* 19:339–349 (1980).

Turner, et al., "p–Amidino Esters a Irreversible Inhibitors of Factor IXa and Xa and Thrombin", *Biochemistry* 25:4929–4935 (1986).

Tsutsumi, et al., "Synthesis and Structure–Activity Relationships of Peptidyl α–Keto Heterocycles as Novel Inhibitors of Prolyl Endopeptidase", *J. Med. Chem.* 37:3492–3502 (1994).

Waxman, et al., "Tick Anticoagulant Peptide (Tap) Is a Novel Inhibitor of Blood Coagulation Factor Xa", *Science* 248:593–596 9 (1990).

Wityak, et al., "Synthesis of Thrombin Inhibitor DuP 714", *J. Org. Chem.* 60:3717–3722 (1995).

Semple, et al., "Design, Synthesis, and Evolution of a Novel, Selective, and Orally Bioavailable Class of Thrombin Inhibitors: P1–argininal derivatives incorporating P3–4 lactam sulfonamide moieties", *J. Med. Chem.* 39:4531–4536 (1996).

Kunitada, et al., "Factor Xa Inhibitors", *Current Pharmaceutical Design*, vol. 2, No. 5, 531–542 (1996).

SELECTIVE FACTOR XA INHIBITORS

This application claims priority of copending provisional application(s) No. 60/084,185 filed on Aug. 11, 1997, which is incorporated herein by reference.

FIELD OF THE INVENTION

This invention relates to a novel class of bicyclic aryl azepinone compounds which are potent and highly selective inhibitors of factor Xa or factor Xa when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin).

BACKGROUND OF THE INVENTION

Blood coagulation protects mammalian species when the integrity of the blood vessel wall is damaged and uncontrolled loss of blood threatens survival. Coagulation, resulting in the clotting of blood, is an important component of hemostasis. Under normal hemostatic circumstances, there is maintained an acute balance of clot formation and clot removal (fibrinolysis). The blood coagulation cascade involves the conversion of a variety of inactive enzymes (zymogens) into active enzymes, which ultimately convert the soluble plasma protein fibrinogen into an insoluble matrix of highly cross-linked fibrin. (See Davie, et al., "The Coagulation Cascade: Initiation, Maintenance and Regulation" *Biochemistry* 30:10363–10370 (1991)). Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

A key enzyme in the coagulation cascade, as well as in hemostasis, is thrombin. Thrombin is intimately involved in the process of thrombus formation, but under normal circumstances can also play an anticoagulant role in hemostasis through its ability to convert protein C into activated protein C in a thrombomodulin-dependent manner. Thrombin plays a central role in thrombosis through its ability to catalyze the penultimate conversion of fibrinogen into fibrin and through its potent platelet activation activity. Direct or indirect inhibition of thrombin activity has been the focus of a variety of recent anticoagulant strategies as reviewed by Claeson "Synthetic Peptides and Peptidomimetics as Substrates and Inhibitors of Thrombin and Other Proteases in the Blood Coagulation System", *Blood Coag. Fibrinol.* 5:411–436 (1994). The major classes of anticoagulants currently used in the clinic directly or indirectly affect thrombin (i.e. heparins, low-molecular weight heparins and coumarins). Thrombin is generated at the convergence of the intrinsic and extrinsic coagulation pathways by the prothrombinase complex. The prothrombinase complex is formed when activated Factor X (factor Xa) and its non-enzymatic cofactor, factor Va assemble on phospholipid surfaces in a $Ca^{+2}$-dependent fashion as reviewed by Mann, et al., "Surface-Dependent Reactions of the Vitamin K-Dependent Enzymes", *Blood* 76:1–16 (1990). The prothrombinase complex converts the zymogen prothrombin into the active procoagulant thrombin.

The location of the prothrombinase complex at the convergence of the intrinsic and extrinsic coagulation pathways, and the significant amplification of thrombin generation (393,000-fold over uncomplexed factor Xa) mediated by the complex at a limited number of targeted catalytic units present at vascular lesion sites, suggests that inhibition of thrombin generation is an ideal method to block uncontrolled procoagulant activity. Unlike thrombin, which acts on a variety of protein substrates as well as at a specific receptor, factor Xa appears to have a single physiologic substrate, namely prothrombin.

Plasma contains an endogenous inhibitor of both the factor VIIa-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVIIa/TFPI/fXa as described by Girard, et al., "Functional Significance of the Kunitz-type Inhibitory Domains of Lipoprotein-associated Coagulation Inhibitor", *Nature* 338:518–520 (1989).

Polypeptides derived from hematophagous organisms have been reported which are highly potent and specific inhibitors of factor Xa. U.S. Pat. No. 4,588,587 awarded to Gasic, describes anticoagulant activity in the saliva of the Mexican leech, *Haementeria officinalis*. A principal component of this saliva is shown to be the polypeptide factor Xa inhibitor, antistasin, by Nutt, et al., "The Amino Acid Sequence of Antistasin, a Potent Inhibitor of Factor Xa Reveals a Repeated Internal Structure", *J. Biol. Chem.* 263:10162–10167 (1988).

Another potent and highly specific inhibitor of Factor Xa, tick anticoagulant peptide, has been isolated from the whole body extract of the soft tick *Ornithidoros moubata*, as reported by Waxman, et al., "Tick Anticoagulant Peptide (TAP) is a Novel Inhibitor of Blood Coagulation Factor Xa", *Science* 248:593–596 (1990).

Other polypeptide type inhibitors of factor Xa have been reported including the following citations by: Condra, et al., "Isolation and Structural Characterization of a Potent Inhibitor of Coagulation Factor Xa from the Leech *Haementeria ghilianii*", *Thromb. Haemost.* 61:437–441 (1989); Blankenship, et al., "Amino Acid Sequence of Ghilanten: Anti-coagulant-antimetastatic Principle of the South American Leech, *Haementeria ghilianii*", *Biochem. Biophys. Res. Commun.* 166:1384–1389 (1990); Brankamp, et al., "Ghilantens: Anticoagulants, Antimetastatic Proteins from the South American Leech *Haementeria ghilianii*", *J. Lab. Clin. Med.* 115:89–97 (1990); Jacobs, et al., "Isolation and Characterization of a Coagulation Factor Xa Inhibitor from Black Fly Salivary Glands", *Thromb. Haemost.* 64:235–238 (1990); Rigbi, et al., "Bovine Factor Xa Inhibiting Factor and Pharmaceutical Compositions Containing the Same", European Patent Application, 352,903 (1990); Cox, "Coagulation Factor X Inhibitor From the Hundred-pace Snake *Deinagkistrodon acutus* venom", *Toxicon* 31:1445–1457 (1993); Cappello, et al., "Ancylostoma Factor Xa Inhibitor: Partial Purification and its Identification as a Major Hookworm-derived Anticoagulant In Vitro", *J. Infect. Dis.* 167:1474–1477 (1993); Seymour, et al., "Ecotin is a Potent Anticoagulant and Reversible Tight-binding khibitor of Factor Xa", *Biochemistry* 33:3949–3958 (1994).

Factor Xa inhibitory compounds which are not large polypeptide-type inhibitors have also been reported including: Tidwell, et al., "Strategies for Anticoagulation With Synthetic Protease Inhibitors. Xa Inhibitors Versus Thrombin Inhibitors", *Thromb. Res.* 19:339–349 (1980); Turner, et al., "p-Amidino Esters as Irreversible Inhibitors of Factor IXa and Xa and Thrombin", *Biochemistry* 25:4929–4935 (1986); Hitomi, et al., "Inhibitory Effect of New Synthetic Protease Inhibitor (FUT-175) on the Coagulation System", *Haemostasis* 15:164–168 (1985); Sturzebecher, et al., "Synthetic Inhibitors of Bovine Factor Xa and Thrombin. Comparison of Their Anticoagulant Efficiency", *Thromb. Res.* 54:245–252 (1989); Kam, et al., "Mechanism Based Isocoumarin Inhibitors for Trypsin and Blood Coagulation Serine Proteases: New Anticoagulants", *Biochemistry* 27:2547–2557 (1988); Hauptmann, et al., "Comparison of the Anticoagulant and Antithrombotic Effects of Synthetic Thrombin and Factor Xa Inhibitors", *Thromb. Haemost.* 63:220–223 (1990); Miyadera, et al., Japanese Patent Application JP 6327488 (1994); Nagahara, et al., "Dibasic (Amidinoaryl)propanoic Acid Derivatives as Novel Blood Coagulation Factor Xa Inhibitors", *J. Med. Chem.* 37:1200–1207 (1994); Vlasuk, et al., "Inhibitors of Thrombosis", WO 93/15756; and Brunck, et al., "Novel Inhibitors of Factor Xa", WO 94/13693. Al-obeidi, et al., "Factor Xa Inhibitors", WO 95/29189, discloses pentapeptide X1-Y-I-R-X2 derivatives as factor Xa inhibitors. Said compounds are useful for inhibiting blood clotting in the treatment of thrombosis, stroke, and myocardial infarction.

SUMMARY OF THE INVENTION

The present invention relates to novel peptide mimetic analogs, their pharmaceutically acceptable isomers, salts, hydrates, solvates and prodrug derivatives.

In another aspect, the present invention includes pharmaceutical compositions comprising a pharmaceutically effective amount of the compounds of this invention and a pharmaceutically acceptable carrier. These compositions are useful as potent and specific inhibitors of blood coagulation in mammals.

In yet another aspect, the invention relates to methods of using these inhibitors as therapeutic agents for disease states in mammals which have disorders of coagulation such as in the treatment or prevention of unstable angina, refractory angina, myocardial infarction, transient ischemnic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. These compositions may optionally include anticoagulants, antiplatelet agents, and thrombolytic agents.

In other aspects of the invention compounds are provided which are useful as diagnostic reagents.

In preferred embodiments, the present invention provides compounds of general formula I:

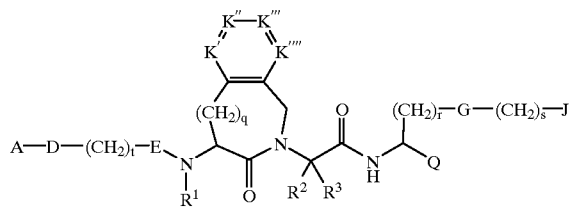

(I)

Wherein:

$R^1$ and $R^2$ are independently selected from the group consisting of H, $C_{1-6}$alkyl, $C_{3-8}$cycloalkyl, $C_{1-3}$alkylaryl, $C_{1-3}$alkyl-$C_{3-8}$cycloalkyl and aryl;

$R^3$ is H, $C_{1-6}$alkyl, or $R^2$ and $R^3$ are taken together to form a carbocyclic ring;

q is an integer from 0–2;

r is an integer from 0–4;

s is an integer from 0–1;

t is an integer from 0–4;

A is selected from the group consisting of $R^8$, $-NR^8R^9$,

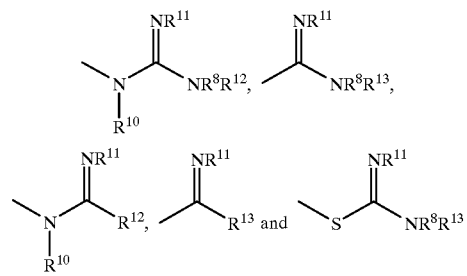

where $R^8$, $R^9$, $R^{10}$ and $R^{11}$ are independently selected from the group consisting of H, $-OH$, $C_{1-6}$alkyl, aryl and $C_{1-4}$alkylaryl; $R^{12}$ is selected from the group consisting of H, $C_{1-6}$alkyl, aryl and $C_{1-4}$alkylaryl, or can be taken together with $R^{10}$ or $R^{11}$ to form a 5–6 membered ring; and $R^{13}$ is selected from the group consisting of H, $C_{1-4}$alkyl, aryl and $C_{1-4}$alkylaryl, or can be taken together with $R^{11}$ to form a 5–6 membered ring;

D is selected from the group consisting of a direct link, $C_{3-8}$cycloalkyl, $C_{1-6}$alkenyl, $C_{1-6}$alkenylaryl, aryl and a five to ten membered heterocyclic ring system containing 1–4 heteroatoms selected from the group consisting of N, O and S;

E is selected from the group consisting of a direct link, $-CO-$, $-SO_2-$, $-O-CO-$, $-NR^{14}-SO_2-$ and $-NR^{14}-CO-$, where $R^{14}$ is selected from the group consisting of H, $-OH$, $C_{1-6}$alkyl, aryl and $C_{1-4}$alkylaryl;

G is selected from the group consisting of a direct link, $C_{3-8}$cycloalkyl, aryl, and a five to ten membered heterocyclic ring system containing 1–4 heteroatoms selected from the group consisting of N, O and S;

J is selected from the group consisting of $R^{15}$, $-NR^{15}R^{16}$,

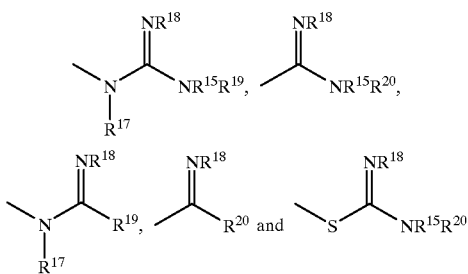

where $R^{15}$, $R^{16}$, $R^{17}$ and $R^{18}$ are independently selected from the group consisting of H, —OH, $C_{1-6}$alkyl, aryl and $C_{1-4}$alkylaryl; $R^{19}$ is selected from the group consisting of H, $C_{1-6}$alkyl, aryl and $C_{1-4}$alkylaryl, or can be taken together with $R^{17}$ or $R^{18}$ to form a 5–6 membered ring; and $R^{20}$ is selected from the group consisting of H, $C_{1-6}$alkyl, aryl and $C_{1-4}$alkylaryl, or can be taken together with $R^{18}$ to form a 5–6 membered ring; with the proviso that when J is $R^{15}$, then G must contain at least one N atom;

K', K", K''' and K"" are independently selected from the group consisting of —CH—, —CR$^4$—, —CR$^5$— and —N—; with the proviso that no more than one of K', K", K''' and K"" are —CR$^4$— and no more than one of K', K", K''' and K"" are —CR$^5$—;

$R^4$ and $R^5$ are independently selected from the group consisting of $C_{1-6}$alkyl, aryl, $C_{1-6}$alkylaryl, $C_{1-4}$alkyloxy, halogen, —NO$_2$, —NR$^6$R$^7$, —NR$^6$COR$^7$, —OR$^6$, —OCOR$^6$, —COOR$^6$, —CONR$^6$R$^7$, —CN, —CF$_3$, —SO$_2$NR$^6$R$^7$ and $C_{1-6}$alkyl—OR$^6$; where $R^6$ and $R^7$ are independently selected from the group consisting of H, $C_{1-6}$alkyl, $C_{1-3}$alkylaryl and aryl;

Q is selected from the group consisting of H,

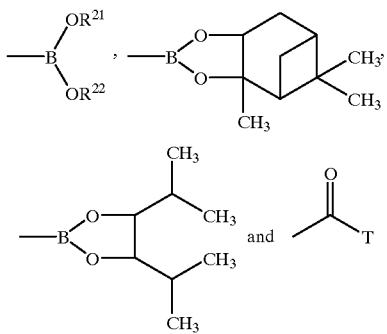

where $R^{21}$ and $R^{22}$ are independently selected from the group consisting of H, $C_{1-3}$alkyl and aryl; and T is selected from the group consisting of H, —COOR$^{23}$, -CONR$^{23}$R$^{24}$, —CF$_3$, —CF$_2$CF$_3$ and a group having the formula:

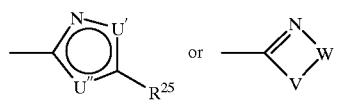

where: $R^{23}$ and $R^{24}$ are independently selected from the group consisting of H, $C_{1-6}$alkyl, aryl and $C_{1-4}$alkylaryl; U' and U" are independently selected from the group consisting of —O—, —S—, —N— and —NH—; with the proviso that at least one of U' or U" is —N— or —NH—; $R^{25}$ is selected from the group consisting of H, $C_{1-6}$alkyl, $C_{2-6}$alkenyl, $C_{0-6}$alkylaryl, $C_{2-6}$alkenylaryl, $C_{0-6}$alkylheterocyclo, $C_{2-6}$alkenylheterocyclo, —CF$_3$ and —CF$_2$CF$_3$; V is selected from the group consisting of —S—, —SO—, —SO$_2$—, —O— and —NR$^{26}$—, where $R^{26}$ is selected from the group consisting of H, $C_{1-6}$alkyl and benzyl; and W is selected from the group consisting of:

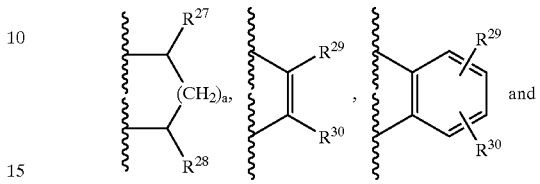

a $C_{6-10}$ heterocyclic ring system substituted by $R^{29}$ and $R^{30}$ and containing 1–4 heteroatoms selected from N, S and O; where: a is an integer from 0–2; $R^{27}$ and $R^{28}$ are independently selected from the group consisting of H, $C_{1-6}$alkyl, aryl, $C_{1-6}$alkylaryl, —COOR$^{31}$, —CONR$^{31}$R$^{32}$, —CN and —CF$_3$; and $R^{29}$ and $R^{30}$ are independently selected from the group consisting of H, $C_{1-6}$alkyl, aryl, $C_{1-6}$alkylaryl, $C_{1-4}$alkyloxy, halogen, —NO$_2$, —NR$^{31}$R$^{32}$, —NR$^{31}$COR$^{32}$, —OR$^{31}$, —OCOR$^{31}$, —COOR$^{31}$, —CONR$^{31}$R$^{32}$, —CN, —CF$_3$, —SO$_2$NR$^{31}$R$^{32}$ and $C_{1-6}$alkyl—OR$^{31}$; where $R^{31}$ and $R^{32}$ are independently selected from the group consisting of H, $C_{1-6}$alkyl, $C_{1-3}$alkylaryl and aryl; and all pharmaceutically acceptable salts and optical isomers thereof.

DETAILED DESCRIPTION OF THE INVENTION

Definitions

In accordance with the present invention and as used herein, the following terms are defined with the following meanings, unless explicitly stated otherwise.

The term "alkyl" refers to saturated aliphatic groups including straight-chain, branched-chain, cyclic groups, and combinations thereof, having the number of carbon atoms specified, or if no number is specified, having up to 12 carbon atoms. The term "cycloalkyl" refers to a mono-, bi-, or tricyclic aliphatic ring having 3 to 12 carbon atoms, preferably 3 to 7 carbon atoms.

The term "alkenyl" refers to unsaturated aliphatic groups including straight-chain, branched-chain, cyclic groups, and combinations thereof, having at least one double bond and having the number of carbon atoms specified.

The term "aryl" refers to an unsubstituted or substituted aromatic ring(s), substituted with one, two or three substituents such as, by way of example and not limitation, $C_{1-6}$alkoxy, $C_{1-6}$alkyl, $C_{1-6}$alkylamino, hydroxy, halogen, cyano (—CN), mercapto, nitro (—NO$_2$), thioalkoxy, carboxaldehyde, carboxyl, carboalkoxy, carboxamide, —NR'R", —NR'COR", —OR, —OCOR, —COOR, —CONR'R", —CF$_3$, —SO$_2$NR'R" and $C_{1-6}$alkyl—OR; aryl, $C_{1-6}$alkylaryl (where the R groups can be H, $C_{1-6}$alkyl, $C_{1-3}$alkylaryl and aryl), including but not limited to carbocyclic aryl, heterocyclic aryl, biaryl and triaryl groups and the like, all of which may be optionally substituted. Preferred aryl groups include phenyl, halophenyl, $C_{1-6}$alkylphenyl, naphthyl, biphenyl, phenanthrenyl, naphthacenyl, and aromatic heterocyclics or heteroaryls, the latter of which is an aryl group containing one to four heteroatoms selected from the group consisting of nitrogen, oxygen and sulfur. Aryl groups preferably have 5–14 carbon atoms making up the ring(s) structure, while heteroaryls preferably have 1–4 heteroatoms, with the remaining 4–10 atoms being carbon atoms.

The terms "heterocyclo" and "heterocyclic ring system" as used herein refer to any saturated or unsaturated monom or bicyclic ring system, containing from one to four heteroatoms, selected from the group consisting of nitrogen, oxygen and sulfur. A typical heterocyclic ring system will have five to ten members, 1–4 of which are heteroatoms. Typical examples of monocyclic ring systems include piperidinyl, pyrrolidinyl, pyridinyl, piperidonyl, pyrrolidonyl and thiazolyl, while examples of bicyclic ring systems include benzimidazolyl, benzothiazolyl and benzoxazolyl, all of which may be substituted.

The term "carbocyclic ring" as used herein refers to any saturated or unsaturated ring containing from three to six carbon atoms.

The terms "alkylaryl" and "alkenylaryl" as used herein refer to an alkyl group or alkenyl group, respectively, having the number of carbon atoms designated, appended to one, two, or three aryl groups. The term benzyl as used herein refers to —$CH_2$—$C_6H_5$.

The term "alkyloxy" as used herein refers to an allyl group linked to an oxygen atom, such as methoxy, ethoxy, and so forth.

The term "halogen" as used herein refer to Cl, Br, F or I substituents.

The term "direct link" as used herein refers to a bond directly linking the substituents on each side of the direct link. When two adjacent substituents are defined as each being a "direct link", it is considered to be a single bond.

Two substituents are "taken together to form a 5–6 membered ring" means that an ethylene or a propylene bridge, respectively, is formed between the two substituents.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, and aluminum bases, and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it. The biological properties of the compounds of the present invention can be readily characterized by the methods described in Examples 13 and 14 and by such other methods as are well known in the art.

In addition, the following abbreviations are used in this application:

"Bn" refers to benzyl.

"Boc" refers to t-butoxycarbonyl.

"BOP" refers to benzotriazol-1-yloxy-tris-(dimethylamino) phosphonium hexafluorophosphate.

"Bu" refers to butyl.

"CBZ" refers to carbobenzyloxy.

"DCM" refers to dichloromethane.

"DIEA" refers to diisopropylethylamine.

"DMF" refers to N,N-dimethylformamide.

"EDC" refers to 1-(3-imethylainopropyl)-3-thylcarbodiimide hydrochloride

"Et" refers to ethyl.

"$Et_2O$" refers to diethyl ether.

"EtOAc" refers to ethyl acetate.

"EtOH" refers to ethanol.

"HF" refers to hydrogen fluoride.

"Me" refers to methyl.

"MeOH" refers to methanol.

"NHS" refers to N-hydroxysuccinimide.

"Ph" refers to phenyl.

"p-TsOH" refers to p-toluenesulfonic acid monohydrate.

"TFA" refers to trifluoroacetic acid.

"THF" refers to tetrahydrofuran.

"Tos" refers to ptoluenesulfonyl.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In the processes described above, the final products may, in some cases, contain a small amount of diastereomeric or enantiomeric products; however, these products do not affect their therapeutic or diagnostic application.

In all of the peptides of the invention, one or more amide linkages (—CO—NH—) may optionally be replaced with another linkage which is an isostere such as —CH$_2$NH—, —CH$_2$S—, —CH$_2$—O—, —CH$_2$CH$_2$—, —CH=CH— (cis and trans), —COCH$_2$—, —CH(OH)CH$_2$—, —CH$_2$SO—, and —CH$_2$SO$_2$—. This replacement can be made by methods known in the art. The following references describe preparation of peptide analogs which include these alternative-linking moieties: Spatola, "Peptide Backbone Modifications" (general review) *Vega Data,* Vol. 1, Issue 3, (March 1983); Spatola, "Chemistry and Biochemistry of Amino Acids, Peptides and Proteins," (general review) B. Weinstein, eds., Marcel Dekker, New York, p. 267 (1983); Morley, *Trends Pharm. Sci.* (general review) pp. 463–468 (1980); Hudson, et al., *Int. J. Pept. Prot. Res.* 14:177–185 (1979) (—CH$_2$NH—, —CH$_2$CH$_2$—); Spatola, et al., *Life Sci.* 38:1243–1249 (1986) (—CH$_2$—S); Hann,*J. Chem. Soc. Perkin Trans. I* pp.307–314 (1982) (—CH=CH—, cis and trans); Almquist, et al.,*J. Med. Chem.* 23:1392–1398 (1980) (—COCH$_2$—); Jennings-White, et al., *Tetrahedron Lett.* 23:2533 (—COCH$_2$—) (1982); Szelke, et al., European Application EP 45665; CA:97:39405 (1982) (—CH(OH) CH$_2$—); Holladay, et al., *Tetrahedron Lett* 24:4401–4404 (1983) (—CH(OH)CH$_2$—); and Hruby, *Life Sci.* 31:189–199 (1982) (—CH$_2$—S—).

PREFERRED EMBODIMENTS

This invention relates to a new class of bicyclic aryl azepinone compounds selected from those of general formula I which are potent and specific inhibitors of Xa, their pharmaceutically acceptable compositions thereof, and the methods of using them as therapeutic agents for disease states in mammals characterized by abnormal thrombosis:

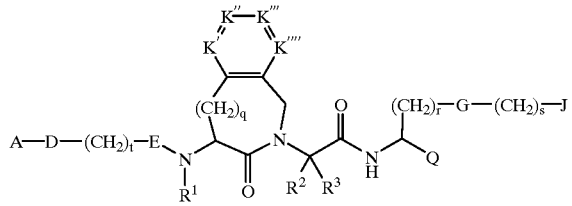

(I)

Wherein:

R$^1$ and R$^2$ are independently selected from the group consisting of H, C$_{1-6}$alkyl, C$_{3-8}$cycloalkyl, C$_{1-3}$alkylaryl, C$_{1-3}$alkyl-C$_{3-8}$cycloalkyl and aryl;

R$^3$ is H, C$_{1-6}$alkyl, or R$^2$ and R$^3$ are taken together to form a carbocyclic ring;

q is an integer from 0–2;

r is an integer from 0–4;

s is an integer from 0–1;

t is an integer from 0–4;

A is selected from the group consisting of R$^8$, —NR$^8$R$^9$,

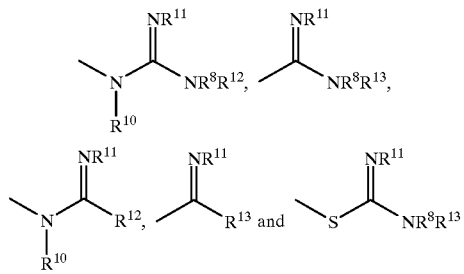

where R$^8$, R$^9$, R$^{10}$ and R$^{11}$ are independently selected from the group consisting of H, —OH, C$_{1-6}$alkyl, aryl and C$_{1-4}$alkylaryl; R$^{12}$ is selected from the group consisting of H, C$_{1-6}$alkyl, aryl and C$_{1-4}$alkylaxyl, or can be taken together with R$^{10}$ or R$^{11}$ to form a 5–6 membered ring; and R$^{13}$ is selected from the group consisting of H, C$_{1-6}$alkyl, aryl and C$_{1-4}$alkylaryl, or can be taken together with R$^{11}$ to form a 5–6 membered ring;

D is selected from the group consisting of a direct link, C$_{3-8}$cycloalkyl, C$_{1-6}$alkenyl, C$_{1-6}$alkenylaryl, aryl and a five to ten membered heterocyclic ring system containing 1–4 heteroatoms selected from the group consisting of N, O and S;

E is selected from the group consisting of a direct link, —CO—, —SO$_2$—, —O—CO—, —NR$^{14}$—SO$_2$— and —NR$^{14}$—CO—, where R$^{14}$ is selected from the group consisting of H, —OH, C$_{1-6}$alkyl, aryl and C$_{1-4}$alkylaryl;

G is selected from the group consisting of a direct link, C$_{3-8}$cycloaikyl, aryl, and a five to ten membered heterocyclic ring system containing 1–4 heteroatoms selected from the group consisting of N, O and S;

J is selected from the group consisting of R$^{15}$, —NR$^{15}$R$^{16}$,

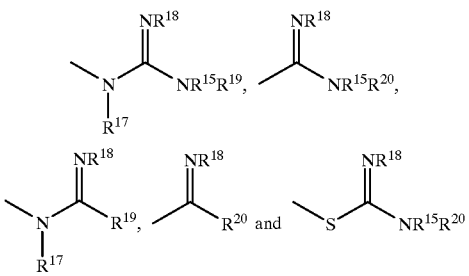

where R$^{15}$, R$^{16}$, R$^{17}$ and R$^{18}$ are independently selected from the group consisting of H, —OH, C$_{1-6}$alkyl, aryl and C$_{1-4}$alkylaryl; R$^{19}$ is selected from the group consisting of H, C$_{1-6}$alkyl, aryl and C$_{1-4}$alkylaryl, or can be taken together with R$^{17}$ or R$^{18}$ to form a 5–6 membered ring; and R$^{20}$ is selected from the group consisting of H, C$_{1-6}$alkyl, aryl and C$_{1-4}$alkylaryl, or can be taken together with R$^{18}$ to form a 5–6 membered ring; with the proviso that when J is R$^{15}$, then G must contain at least one N atom;

K', K", K'" and K""are independently selected from the group consisting of —CH—, —CR$^4$—, —CR$^5$— and —N—; with the proviso that no more than one of K', K", K'" and K"" are —CR$^4$— and no more than one of K', K", K'" and K"" are —CR$^5$—;

R$^4$ and R$^5$ are independently selected from the group consisting of C$_{1-6}$alkyl, aryl, C$_{1-6}$alkylaryl, $C_{1-4}$alkyloxy, halogen, —$NO_2$, —$NR^6R^7$, —$NR^6COR^7$, —$OR^6$, —$OCOR^6$, —$COOR^6$, —$CONR^6R^7$, —CN, —$CF_3$, —$SO_2NR^6R^7$ and $C_{1-6}$alkyl—$OR^6$; where $R^6$ and $R^7$ are independently selected from the group consisting of H, $C_{1-6}$alkyl, $C_{1-3}$alkylaryl and aryl;

Q is selected from the group consisting of H,

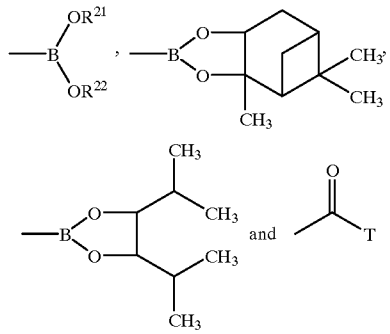

where $R^{21}$ and $R^{22}$ are independently selected from the group consisting of H, $C_{1-3}$alkyl and aryl; and T is selected from the group consisting of H, —$COOR^{23}$, —$CONR^{23}R^{24}$, —$CF_3$, —$CF_2CF_3$ and a group having the formula:

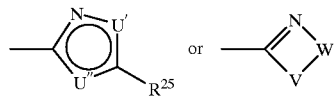

where: $R^{23}$ and $R^{24}$ are independently selected from the group consisting of H, $C_{1-6}$alkyl, aryl and $C_{1-4}$alkylaryl; U' and U" are independently selected from the group consisting of —O—, —S—, —N— and —NH—; with the proviso that at least one of U' or U" is —N— or —NH—; $R^{25}$ is selected from the group consisting of H, $C_{1-6}$alkyl, $C_{2-6}$alkenyl, $C_{0-6}$alkylaryl, $C_{2-6}$alkenylaryl, $C_{0-6}$alkylheterocyclo, $C_{2-6}$alkenylheterocyclo, —$CF_3$ and —$CF_2CF_3$; V is selected from the group consisting of —S—, —SO—, —$SO_2$—, —O— and —$NR^{26}$—, where $R^{26}$ is selected from the group consisting of H, $C_{1-6}$alkyl and benzyl; and W is selected from the group consisting of:

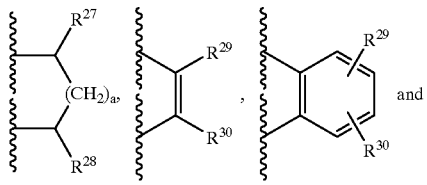

a $C_{6-10}$ heterocyclic ring system substituted by $R^{29}$ and $R^{30}$ and containing 1–4 heteroatoms selected from N, S and O; where: a is an integer from 0–2; $R^{27}$ and $R^{28}$ are independently selected from the group consisting of H, $C_{1-6}$alkyl, aryl, $C_{1-6}$alkylaryl, —$COOR^{31}$, —$CONR^{31}R^{32}$, —CN and —$CF_3$; and $R^{29}$ and $R^{30}$ are independently selected from the group consisting of H, $C_{1-6}$alkyl, aryl, $C_{1-6}$alkylaryl, $C_{1-4}$alkyloxy, halogen, —$NO_2$, —$NR^{31}R^{32}$, —$NR^{31}COR^{32}$, —$OR^{31}$, —$OCOR^{31}$, —$COOR^{31}$, —$CONR^{31}R^{32}$, —CN, —$CF_3$, —$SO_2NR^{31}R^{32}$ and $C_{1-6}$alkyl—$OR^{31}$; where $R^{31}$ and $R^{32}$ are independently selected from the group consisting of H, $C_{1-6}$alkyl, $C_{1-3}$alkylaryl and aryl; and all pharmaceutically acceptable salts and optical isomers thereof.

A preferred embodiment of compounds of general structural formula I have the following stereochemistry:

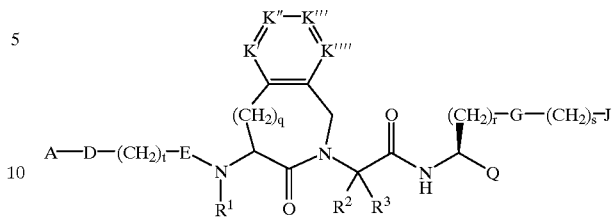

Preferred $R^1$ and $R^2$ substituents are H and $C_{1-6}$alkyl; more preferably H and methyl; most preferably H. $R^3$ is preferably H.

The integer "r" is preferably 3.

The integer "s" is preferably 0.

The integer "t" is preferably from 0–1.

In the various "A" substituents, it is preferred that $R^8$, $R^9$, $R^{10}$ and $R^{11}$ are independently selected from the group consisting of H and $C_{1-6}$alkyl; and are more preferably independently selected from the group consisting of H and methyl. It is also preferred that $R^{12}$ is H, $C_{1-6}$alkyl or taken together with $R^{10}$ or $R^{11}$ to form a 5–6 membered ring; and is more preferably H or methyl. It is also preferred that $R^{13}$ is H, $C_{1-6}$alkyl or taken together with $R^{10}$ to form a 5–6 membered ring; and is more preferably H or methyl.

D is preferably selected from the group consisting of a direct link, $C_{3-8}$cycloalkyl, aryl and a five to ten membered heterocyclic ring system containing 1–4 heteroatoms selected from the group consisting of N, O and S.

E is preferably a direct link, —CO— or —$SO_2$—.

G is preferably a direct link.

In the "J" substituent, it is preferred that $R^{15}$, $R^{16}$, $R^{17}$, $R^{18}$, $R^{19}$ and $R^{20}$ are independently selected from the group consisting of H and $C_{1-6}$alkyl, more preferably H and methyl.

Preferably at least three of K', K", K'" and K"" are —CH—; more preferably K', K", K'" and K"" are all —CH—. When one of the K's are —$CR^4$— or —$CR^5$—, then $R^4$ or $R^5$ is preferably halogen.

Q is preferably:

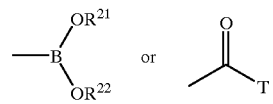

where $R^{21}$ is preferably H and $R^{22}$ is preferably H.

T is preferably H, —$COOR^{23}$, —$CONR^{23}R^{24}$ or a group having the formula:

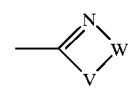

$R^{23}$ is preferably H. $R^{24}$ is preferably $C_{1-4}$alkylaryl. V is-preferably —S—, —O— or —$NR^{26}$—, where $R^{26}$ is preferably H or methyl, more preferably H. W is preferably selected from the group consisting of:

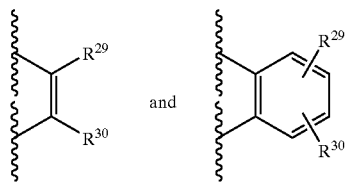

W is more preferably

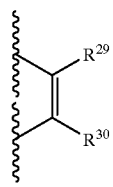

$R^{29}$ and $R^{30}$ are preferably independently selected from the group consisting of H, —O—$R^{31}$, —COO$R^{31}$, —CON$R^{31}R^{32}$ or —CF$_3$; more preferaly H.

When W is:

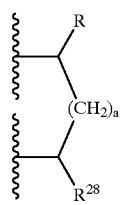

then $R^{27}$ is preferably H and $R^{28}$ is preferably H.

When T is:

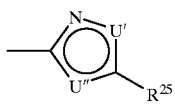

then U' is preferably O, U''' is preferably N and $R^{25}$ is preferably —CF$_3$ or —CF$_2$CF$_3$.

In one preferred embodiment of the invention, s is 0; $R^2$ and $R^3$ are H; K'. K''. K''' and K'''' are —CH—; and Q is —C(O)—T. This is also illustrated as a preferred group of compounds defined by the general structaral formula II as:

(II)

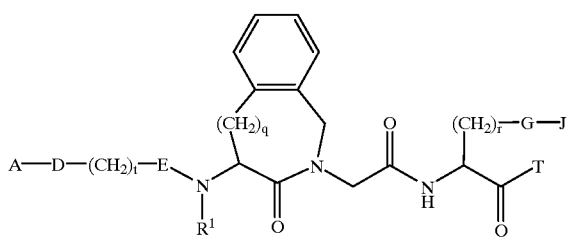

A preferred embodiment of compounds of general structural formula II have the following stereochemistry:

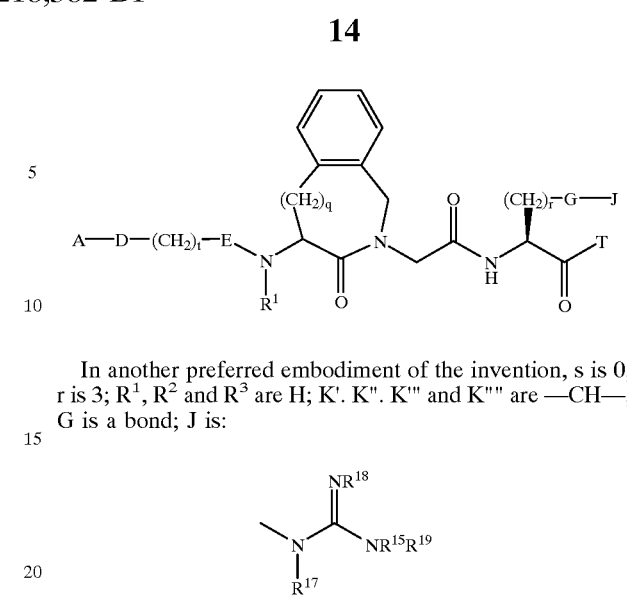

In another preferred embodiment of the invention, s is 0; r is 3; $R^1$, $R^2$ and $R^3$ are H; K'. K''. K''' and K'''' are —CH—; G is a bond; J is:

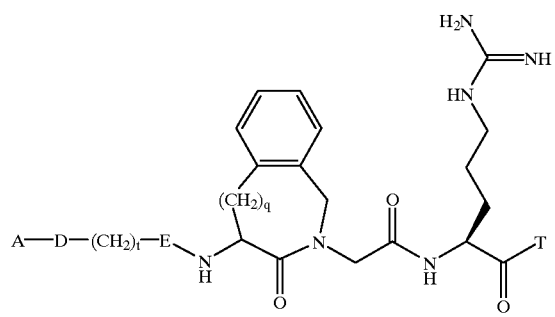

where $R^{15}$, $R^{17}$, $R^{18}$ and $R^{19}$ are all H; and Q is —C(O)—T. This is also illustrated as a preferred group of compounds defied by the general structural formula III as:

(III)

A preferred embodiment of compounds of general structural formula III have the following stereochemistry:

This invention also encompasses all pharmaceutically acceptable isomers, salts, hydrates and solvates of the compounds of formulas I, II and III. In addition, the compounds of formulas I, III and III can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

The following structures are illustrative of the compounds of the present invention and are not intended to be limiting in any manner. It is to be noted that in the compounds of the invention, certain substituents are present between two other substituents. For example, D is positioned between A— and —(CH$_2$)$_t$—E—. Accordingly, substituents such as D are illustrated below as having two "dangling" bonds, the bond on the left representing a direct link to substituent A— and the bond on the right representing a direct link to —(CH$_2$)$_t$—E—. Therefore, the general formula of A—D—(CH$_2$)$_t$—E— where D is phenyl can be written as:

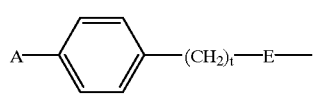

D, a henyl group, would then be written as follows in the tables below:

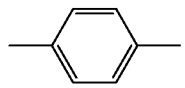

Other substituents in the table below may also be presented as having one or two similar "dangling" bonds. It is understood that these represent direct links to the adjacent substituent(s). It is also understood that the compounds illustrated below can exist as other isomers, and the isomeric form illustrated herein is not intended to be limiting in any manner.

The invention encompasses compounds of general structural formula IV, where $R^1$, $R^2$ and $R^3$ are H; q is 1; r is 3; s is 0; G is a direct link; J is —NH—C(NH)NH$_2$; K', K", K'" and K"" are —CH—; and Q is:

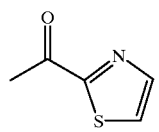

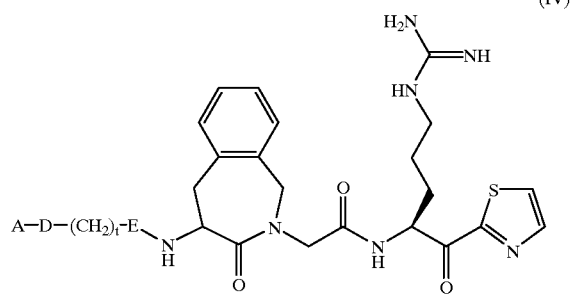

(IV)

| # | A | D | t | E |
|---|---|---|---|---|
| 1 | H— | 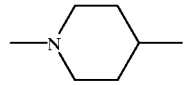 | 2 | —SO$_2$— |
| 2 | H$_3$C— | 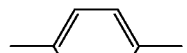 | 1 | —SO$_2$— |
| 3 | H— | 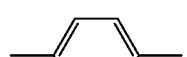 | 1 | direct link |
| 4 | H— | 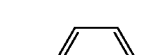 | 1 | —CO— |
| 5 | H$_3$C— | 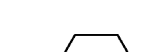 | 2 | —NHSO$_2$— |
| 6 | H$_3$C— | direct link | 0 | —N(CH$_3$)—SO$_2$— |

-continued (IV)

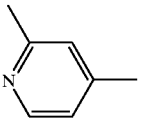

| # | A | D | t | E |
|---|---|---|---|---|
| 7 | H— |  | 2 | —NHCO— |
| 8 | CH₃CH₂— |  | 2 | —NHCO— |
| 9 | 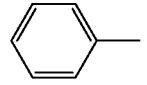 |  | 0 | —SO₂— |
| 10 | (CH₃)₂N— | direct link | 3 | —SO₂— |
| 11 | H— | 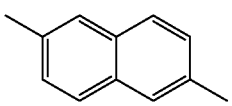 | 0 | —SO₂— |
| 12 | 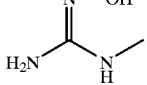 | direct link | 3 | —CO— |
| 13 | 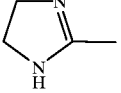 | 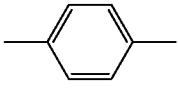 | 1 | —CO— |
| 14 | H— | 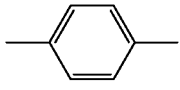 | 1 | direct link |
| 15 | HO— | 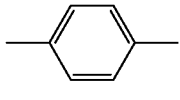 | 2 | direct link |
| 16 | (CH₃)₃C— | 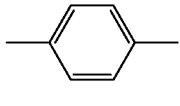 | 0 | —SO₂— |
| 17 | H— | 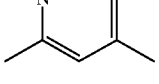 | 2 | —SO₂— |

-continued (IV)

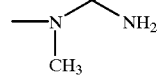

| # | A | D | t | E |
|---|---|---|---|---|
| 18 | H— | 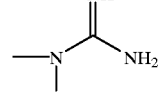 | 0 | —SO₂— |

The invention encompasses compounds of general structural formula V, where $R^1$, $R^2$ and $R^3$ are H; q is 2; t is 1; A is H; D is phenyl; E is —SO₂—; K', K'', K''' and K'''' are —CH—; and Q is

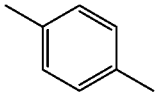

(V)

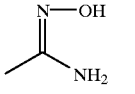

| # | r | G | s | J |
|---|---|---|---|---|
| 1 | 3 | direct link | 0 | (guanidine with N-CH₃) |
| 2 | 3 | direct link | 0 | (guanidine with N-OH) |
| 3 | 1 | (p-phenylene) | 0 | (N-OH amidine) |

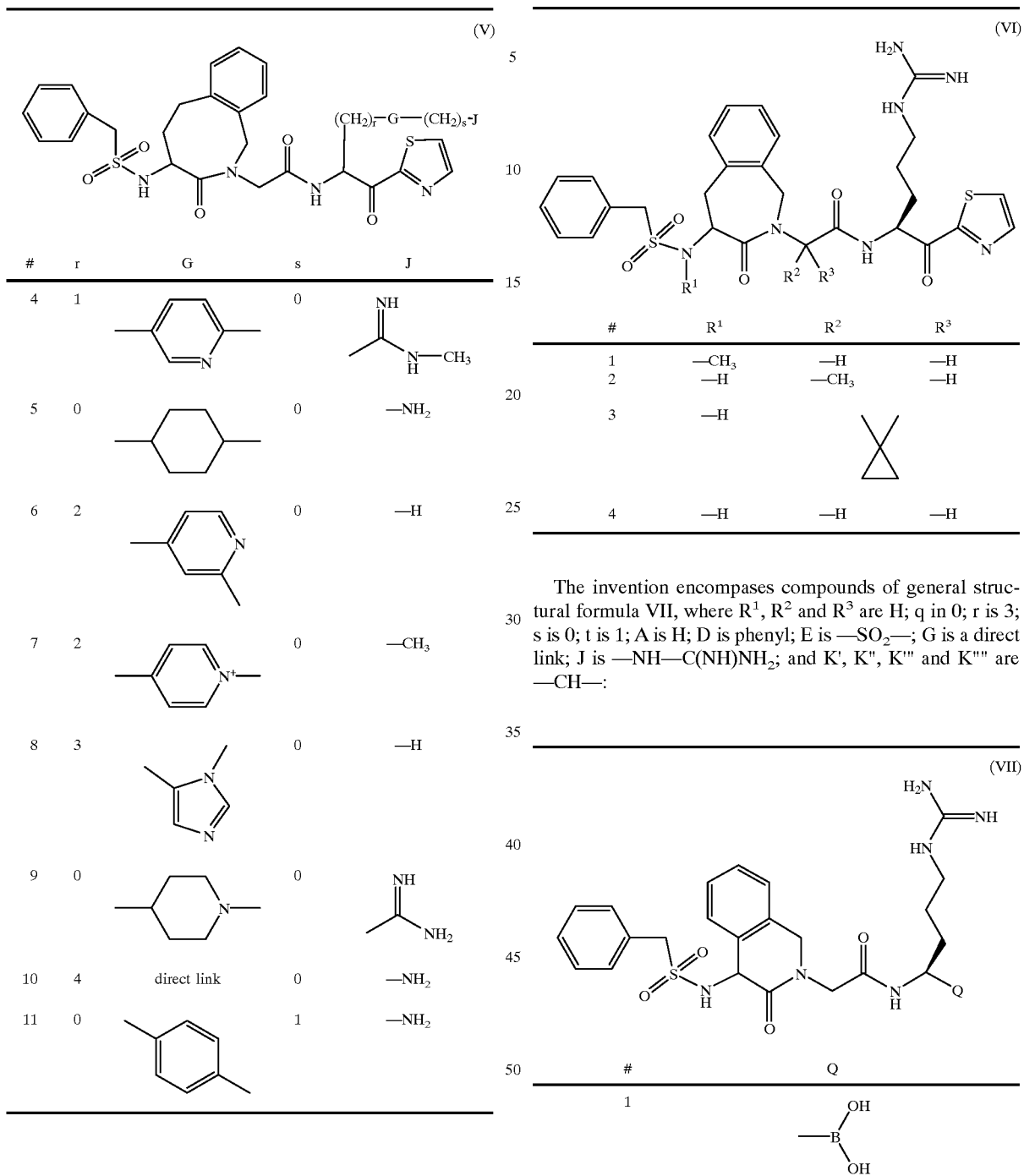

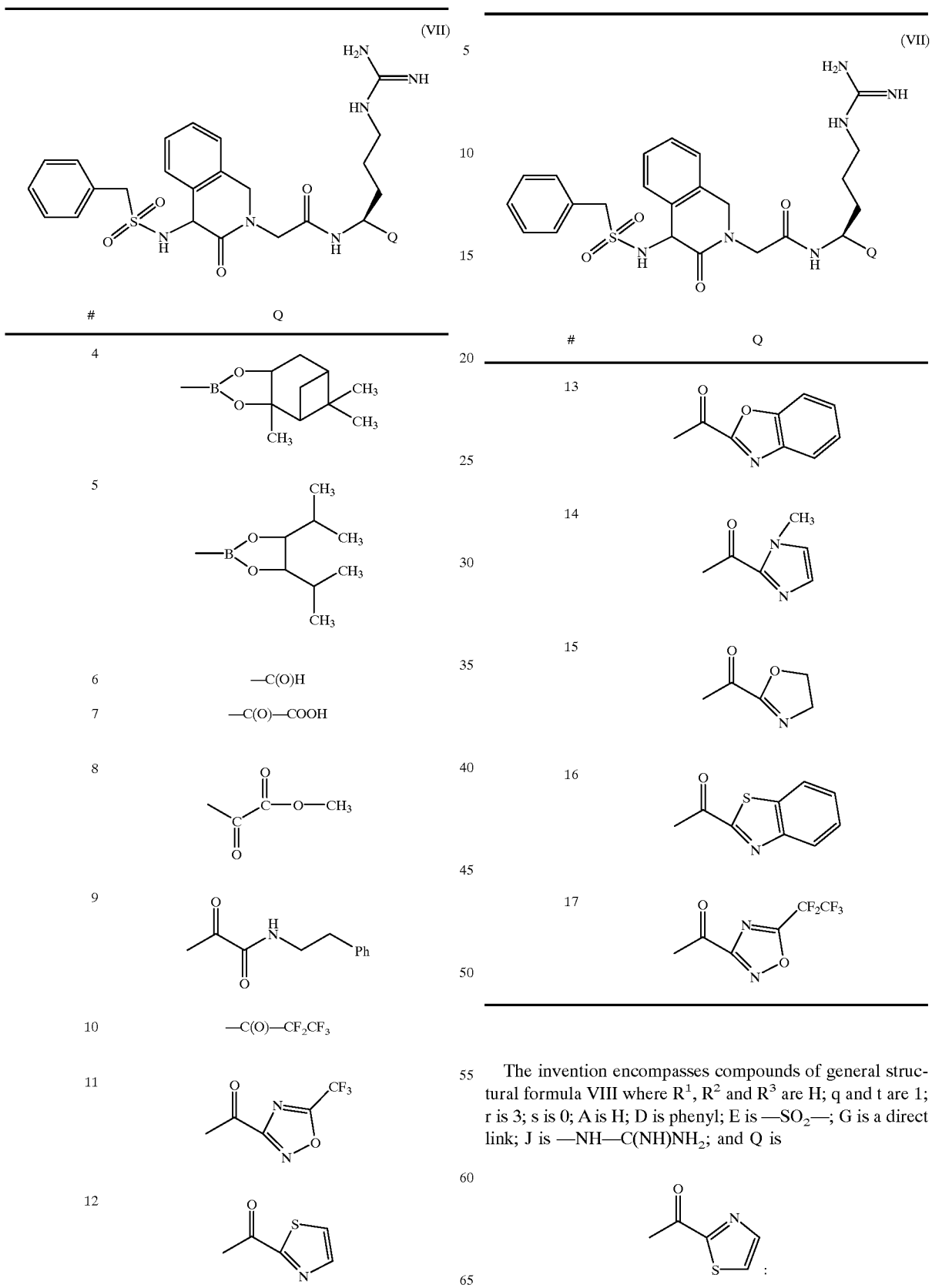
The invention encompasses compounds of general structural formula VIII where $R^1$, $R^2$ and $R^3$ are H; q and t are 1; r is 3; s is 0; A is H; D is phenyl; E is —SO$_2$—; G is a direct link; J is —NH—C(NH)NH$_2$; and Q is
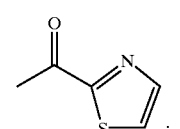:

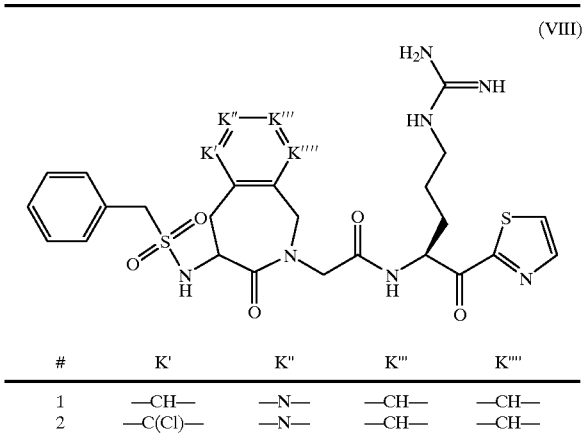

| # | K' | K" | K''' | K'''' |
|---|---|---|---|---|
| 1 | —CH— | —N— | —CH— | —CH— |
| 2 | —C(Cl)— | —N— | —CH— | —CH— |

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successfiul thrombolytic therapy and/or reduce the time to repeifusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, microencapsulation, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamelar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

PREPARATION OF THE DISCLOSED COMPOUNDS

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated. The reaction products are isolated and purified by conventional methods, typically by solvent extraction into a compatible solvent. The products may be further purified by column chromatography or other appropriate methods. Most compounds are purified by reversed-phase HPLC and characterized by ion-spray mass spectrometry.

During the synthesis of these compounds, the functional groups of the amino acid derivatives used in these methods are protected by blocking groups to prevent side reactions during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

The compounds of this invention may be preferably prepared by coupling the carboxylic acid of formula (a) to the amine of formula (b) by the standard amide bond formation strategies:

(a)

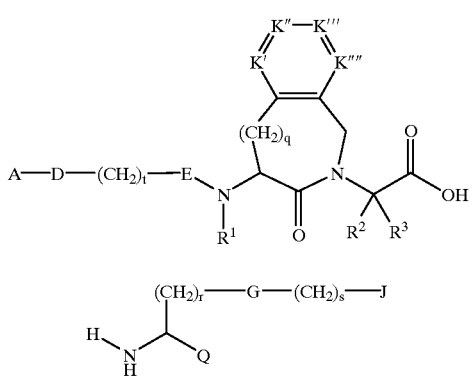

(b)

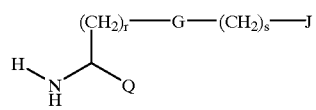

The compounds of formula (b) wherein Q is H can be prepared by the methods disclosed in WO 96/01338; WO 96/24609; Feng, et al., WO 96/31504; and WO 96/32110, the disclosures of which are incorporated herein by reference.

The compounds of formula (b) wherein Q is a boron containing compound can be prepared by the methods disclosed in J. Org. Chem. 60:3717–3722 (1995) and de Nanteuil, et al., EP 688,788, the disclosures of which are incorporated herein by reference.

The compounds of formula (b) wherein Q is —C(O)—T, where T is H, may be prepared by the methods disclosed in WO 93/15756, supra; Vlasuk, et al., WO 94/17817; Abelman, et al., WO 94/21673; Webb, et al., WO 94/08941; Veber, et al., WO 94/25051; Levy, et al., WO 95/35312; Semple, et al., WO 95/35313; Abelman, et al., WO 95/28420; and Abelman, et al., WO 96/19493, the disclosures of which are incorporated herein by reference.

The compounds of formula (b) wherein Q is —C(O)—T, where T is —COOR$^{23}$ or —CONR$^{23}$R$^{24}$, may be prepared by the methods disclosed in WO 94/25051, supra, WO 94/08941, supra, and WO 94/21673, supra, the disclosures of which are incorporated herein by reference.

The compounds of formula (b) wherein Q is —C(O)—T, where T is —CF$_3$ or —CF$_2$CF$_3$, may be prepared by the methods disclosed in Schacht, et al., GB 2287027, the disclosure of which is incorporated herein by reference.

The compounds of formula (b) wherein Q is —C(O)—T, where T is:

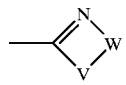

and V is —S—, —O—, —SO— or —SO$_2$— can be readily synthesized by the methods disclosed in Costanzo, et al., U.S. Pat. No. 5,523,308; Di Maio, et al., WO 96/19483; U.S. Pat. No. 5,164,371; J. Am. Chem. Soc. 114: 1854–1863 (1992); J. Med. Chem. 38:76–85 (1995); and J. Med. Chem. 37:3492–3502 (1994). Lastly, fragments where V is —NR$^{21}$—, where R$^{21}$ is H, C$_{1-6}$alkyl or benzyl, can be synthesized by techniques illustrated in J. Med. Chenm 37:3492–3502 (1994). All of these references are incorporated herein by reference.

The compounds of formula (b) wherein Q is —C(O)—T, where T is:

and U' and U" are the various substituents (—O—, —S—, —N—, —NH—) may be prepared by the methods disclosed in J. Med. Chem. 38: 1355–1371 (1995) and J. Med. Chem. 37: 2421–2436 (1994), the disclosures of which are incorporated herein by reference.

The starting compound of formula (a) is either a known compound or can be produced by known methods (Heitsch, et al., Canadian Patent No. 2,071,744; Sugihara, et al., Canadian Patent No. 2,126,026; Baker, et al., EP 365,992; U.S. Pat. No. 4,251,438; Carr, et al., U.S. Pat. No. 4,341, 698; Goldman, et al., U.S. Pat. No. 5,120,718; Biswanath, et al., U.S. Pat. No. 5,164,388; Duggan, et al., U.S. Pat. No. 5,281,585; Sugihara, et al., U.S. Pat. No. 5,294,713; Bovy, et al., WO 95/06038; WO 95/35308; J. Chem. Soc. Perkin Trans. I 1687–1689 (1989); and Int. J. Peptide Protein Res. 37:468–475 (1991)) or can be prepared by the methods shown in the following reaction formulae.

The following reaction scheme provides a more specific illustration of the above reaction formulae. The chemical reactions described below can easily be modified and combined with other techniques that are well known in the art to produce other compounds within the scope of the invention.

Scheme

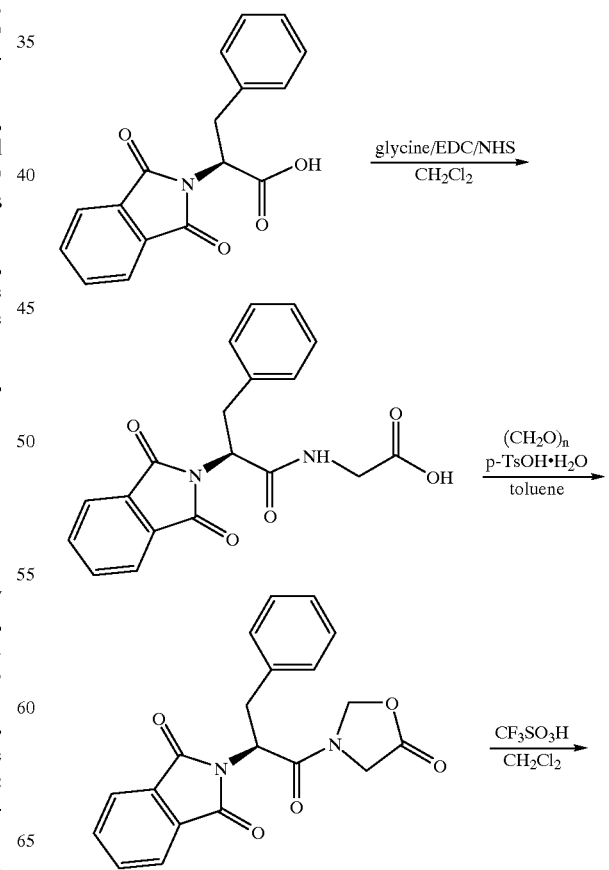

-continued
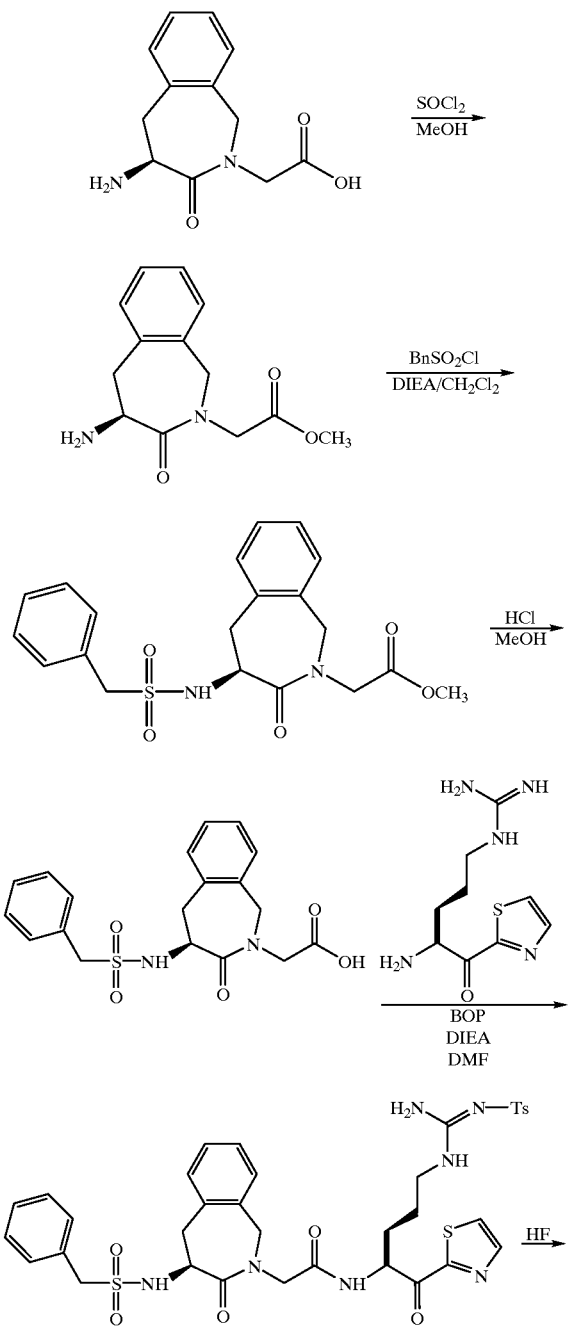
-continued
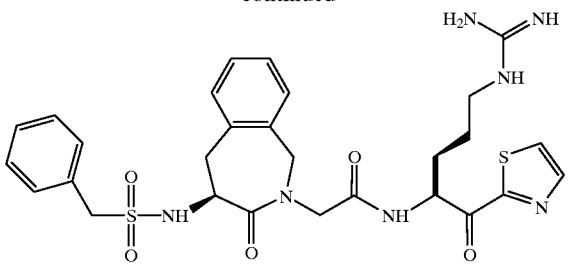
The reagent used in the eighth step of the Scheme can be synthesized as follows:
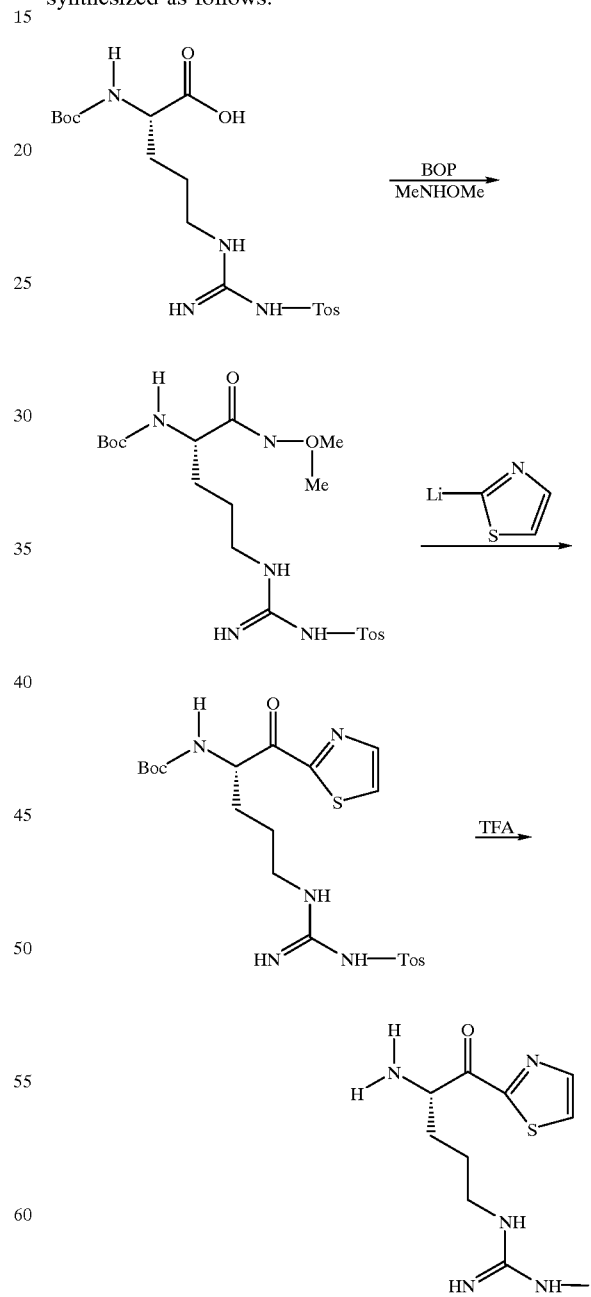
Without further elaboration, it is believed that one skilled in the art can utilize the present invention to its fullest extent. Therefore, the following prefeffed specific embodiments are

EXAMPLE 1

Preparation of:

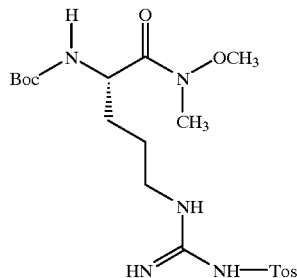

To a suspension of Boc-Arg(Tos)-OH (2 g, 4.7 mmol) in DMF (20 mL) at 0° C. was added MeNHOMe.HCl (1 g, 10.3 mmol), DIEA (6 mL) and BOP (2.5 g, 5.6 mmol). The solution was stirred at 0° C. for 10 hours. DMF was evaporated by vacuum. The oily residue was dissolved in EtOAc (200 mL) and water (20 mL). The organic layer was washed with sat. NaHCO$_3$, water (20 mnL), 1 M HCl ( 10 mL) and sat. NaCl (2×20 mL). The organic layer was dried over MgSO$_4$, filtered and evaporated to give a suspension. The suspension was filtered, and the solid was washed with cold EtOAc (10 mL) and dried to give Boc-Arg(Tos)-N(Me)OMe, shown above, (1.5 g, 70% yield).

FAB-MS $(M+H)+=472$

EXAMPLE 2

Preparation of:

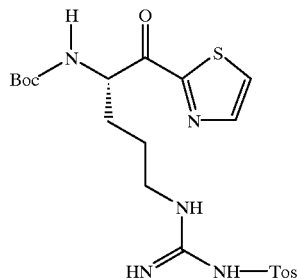

To a solution of thiazole (2.5 g, 29 mmol) in THF (25 mL) at −78° C. was added n-BuLi (1.6 M in hexane, 19 mL) dropwise. The mixture was stirred for 30 minutes. Then a solution of Boc-Arg(Tos)-N(Me)OMe, from Example 1, (1.7 g, 3.6 mmol) in THF (50 mL) was added to the lithiothiazole mixture at −78° C. The solution was stirred for 2 hours. 1M HCl (30 mL) was added to the reaction mixture and warmed to room temperature. The mixture was extracted with EtOAc (100 mL). The organic layer was washed with sat. NaCl (30 mL), dried over MgSO$_4$, filtered and evaporated. The crude oily residue was purified by flash column chromatography over SiO$_2$ (50% EtOAc in CH$_2$Cl$_2$) to give Boc-Arg(Tos)-thiazole, shown above, (1.5 g, 84% yield) as a powder.

DCI-MS $(M+H)+=496$

EXAMPLE 3

Preparation of:

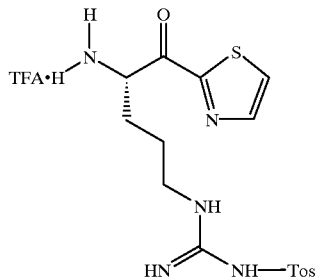

To a solution of Boc-Arg(Tos)-thiazole from Example 2, (300 mg, 0.6 mmol) in CH$_2$Cl$_2$ (10 mL) at 0° C., was added TFA (10 mL). The solution was stirred at 0° C. for 2 hours. The solvent and excess TFA were evaporated to give an oily residue which was then used directly without further purification.

EXAMPLE 4

Preparation of (S)-N-[2-(1,3-Dihydro-1,3-dioxo-2H-isoindol-2-yl)-1-oxo-3-phenylpropyl]glycine:

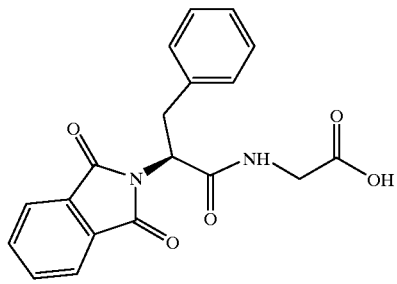

The title compound was prepared as described in *Biopolymers* (38)1–12 (1996) with minor modifications.

A mixture of N-phthaloyl-L-phenylalanine (10.0 g, 33.9 mmol), EDC (15.9 g, 83.0 mmol), and NHS (8.77 g, 76.2 mmol) in DCM (100 mL) was stirred at ambient temperature under argon overnight. The reaction mixture was then concentrated to give a residue, which was taken up in dioxane (100 mL). To this mixture was added a solution of glycine (6.35 g, 84.7 mmol) and sodium bicarbonate (5 g) in water (100 mL), and the reaction was stirred overnight. Most of the solvent was removed by concentration, and the remainder was acidified with 1N HCl to give a white, opaque mixture. This was extracted with EtOAc (3×50 mL), and the combined organics were washed several times with 1N HCl and water, in an alternating manner. The organics were dried over magnesium sulfate and concentrated to give a white solid, which was triturated several times with minimal amounts of Et$_2$O, using filtration to recover the crude desired product as a white solid (9.78 g).

EXAMPLE 5

Preparation of (S)-3-[2-(1,3-Dihydro-1,3-dioxo-2H-isoindol-2-yl)-1-oxo-3-phenylpropyl]-5-oxazolidinone:

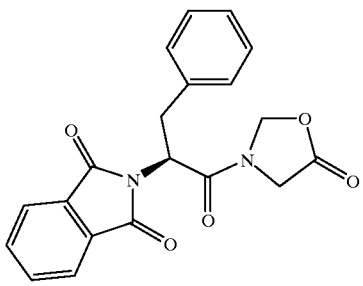

The title compound was prepared as described in *Biopolymers* (38)1–12 (1996) with minor modifications.

A mixture of the dipeptide from Example 4 (9.62 g, 27.3 mmol), paraformaldehyde (20.5 g, 25 equiv.), and p-TsOH (550 mg, 0.1 equiv.) in toluene (555 mL) was heated to reflux using a Dean-Stark water separator. Over the course of 4 hours, three more aliquots of paraformaldehyde (4 g, 5 eq) were added at one hour intervals. After this time, all of the dipeptide starting material had been consumed by TLC analysis. The residue was digested with EtOAc (500 mL) and sat. aqueous sodium bicarbonate (250 mL), and the solids were removed by decanting. The layers were separated, and the organics were washed with sat. sodium bicarbonate and sat. sodium chloride, then dried over magnesium sulfate. Filtration and concentration gave the desired product as an off-white solid (6.77 g). This material was used in the next step without further purification.

EXAMPLE 6

Preparation of (S)-4-(1,3-Dihydro-1,3-dioxo-2H-isoindol-2-yl)-1,3,4,5-tetrahydro-3-oxo-2H-2-benzazepine-2-acetic acid:

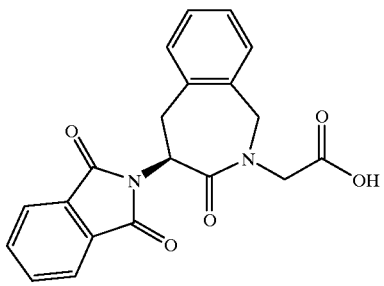

The title compound was prepared as described in *Biopolymers* (38)1–12 (1996).

A solution of the oxazolidinone from Example 5 (924 mg, 2.54 mmol) in dry DCM (6 mL) was treated at ambient temperature with trifluoromethanesulfonic acid (5 g). The reaction mixture turned dark brown, and was stirred overnight at ambient temperature. DCM (50 mL) was added, the mixture was cooled with an ice-water bath, and about 10 g of ice were added. The organic layer was washed with water (2×30 mL) and sat. sodium chloride (50 mL), and then extracted with 6% aqueous sodium bicarbonate (3×50 mL). The aqueous layer was acidified to pH 2 with concentrated HCl, and extracted with DCM (3×50 mL). The organics were dried over sodium sulfate and concentrated to afford a slightly sticky yellow solid. When treated with DCM, the product was able to be isolated as a light yellow powdery solid (799 mg).

EXAMPLE 7

Preparation of (S)-4-Amino-1,3,4,5-tetrahydro-3-oxo-2H-2-benzazepine-2-acetic acid:

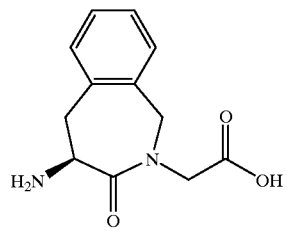

The title compound was prepared as described in *Biopolymers* (38)1–12 (1996).

A solution of the phthalimido acid from Example 6 (720 mg, 1.98 mmol) and hydrazine monohydrate (593 mg, 12 mmol) in absolute ethanol (25 mL) was heated at gentle reflux for 2 hr, then cooled and concentrated. The residue was dissolved in water (20 mL) and the solution was acidified to pH 5 with glacial acetic acid. This mixture was stirred for 1 hr, then filtered to give 180 mg of a white solid, which was determined by HPLC analysis to be a mixture of the desired product and phthaloyl hydrazide. This solid was stirred for 10 min with 1N acetic acid, filtered, and the filtrate was concentrated to give 461 mg of a white solid, which was determined by HPLC to be 90% the desired product and 10% phthaloyl hydrazide. This mixture was used in the next reaction without further purification.

EXAMPLE 8

Preparation of (S)-4-Amino-1,3,4,5-tetrahydro-3-oxo-2H-2-benzazepine-2-acetic acid, methyl ester:

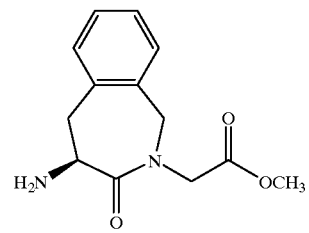

MeOH (5 mL) was cooled with an ice-acetone bath, and thionyl chloride (60 μL) was added. This solution was stirred for 1 min, and then the amino acid from Example 7 (163 mg, 0.70 mmol) was added all at once. After removing the cooling bath, the reaction was stirred while warming to ambient temperature over 1 hr, and then heated to 40° C. for another 1.5 hr. When the reaction mixture was concentrated to dryness, HPLC analysis of the residue indicated that the reaction was incomplete, so the above reaction sequence was repeated, this time heating the reaction for 0.5 hr at the end. The reaction mixture was concentrated to dryness, giving the product as a light yellow solid (168 mg, 97%).

EXAMPLE 9

Preparation of:

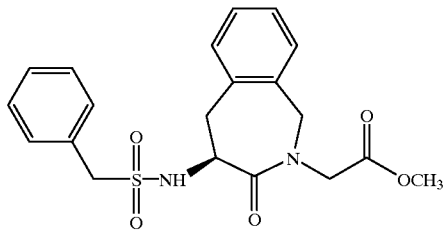

A solution of the amino methyl ester from Example 8 (168 mg, 0.70 mmol) in dichloromethane (5 mL) was cooled to −78° C., and DIEA (410 mL, 3.5 eq) and α-toluenesulfonyl chloride (143 mg, 0.75 mmol) were added. The reaction was then allowed to warm to ambient temperature over 3 hr. The reaction was incomplete, so the reaction was re-ooled to −78° C., and additional α-toluenesulfonyl chloride (52 mg, 0.27 mmol) was added. The reaction was then allowed to stir while warming to ambient temperature overnight. The reaction mixture was concentrated to dryness, and the residue was purified by flash column chromatography on silica gel (30% ethyl acetate in hexane, followed by 50% ethyl acetate in hexane) to give the desired product (182 mg, 67%) as a white solid.

EXAMPLE 10

Preparation of:

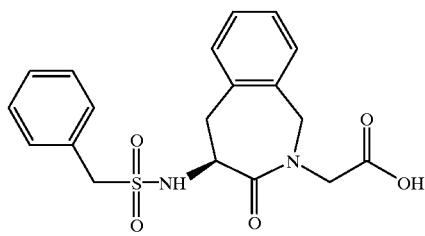

A mixture of the sulfonamide methyl ester from Example 9 (58 mg, 0.14 mmol), 1N HCl (10 mL), and MeOH (3 mL) was heated at 70° C. for 24 hr, following the progress of the reaction by HPLC. When the reaction was complete, the mixture was lyophilized to give a gummy residue. This material was again lyophilized from water (5 mL) to give the desired product in crude form as a solid (85 mg). This material was used in the next step without ftuther purification.

EXAMPLE 11

Preparation of:

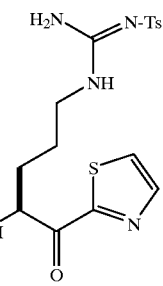

To a solution of Boc-Arg(Tos)-thiazole from Example 2 (89 mg, 0.18 mmol) in DCM (2 mL) was added TFA (2 mL), and the reaction was stirred at ambient temperature for 40 min. Concentration gave a residue which was again taken up in DCM (5 mL) and reconcentrated to give the free amine as the TFA salt. This material was dissolved in DMF (1 mL) and added to a solution of the crude acid from Example 10 in DMF (2 mL). The pH of the solution was raised to 9 with DIEA (200 μL), and the reaction mixture was placed in an ice-water bath. BOP reagent (80 mg, 0.18 mmol) was added, the reaction mixture was checked with pH paper to ensure continued basicity, and it was allowed to stir while warming to ambient temperature overnight. The solution was then partitioned between ethyl acetate (50 mL) and 0.1 N HCl (25 mL), and the organics were washed with sat. sodium bicarbonate (2×25 mL), sat. sodium chloride (25 mL), and finally dried over anhydrous sodium sulfate. Filtration and concentration gave the crude product (105 mg) as an orange solid, which was used in the next reaction without fuirther purification.

*APCI-MS* $(M+H^+)=766$.

EXAMPLE 12

Preparation of Compound VI(4):

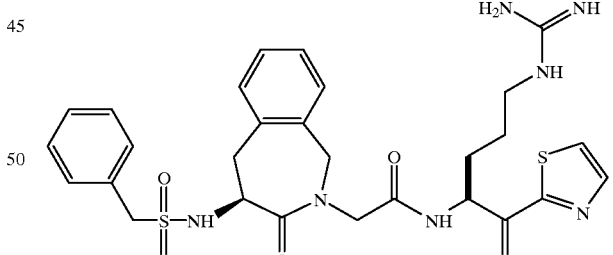

A mixture of the crude product from Example 11, anisole (1 mL), and ethyl methyl sulfide (250 mL) and 500 mg of Merrifield resin was cooled with liquid nitrogen and treated with HF (5 mL). The reaction was allowed to stir for 1 hr in an ice-water bath, then the HF was removed under vacuum. The residue was washed with ether (2×50 mL), and the dry resin was extracted twice with 2M aqueous acetic acid (25 mL, then 5 mL). The aqueous solution was lyophilized to give the crude product as a solid, which was purified by reverse-phase HPLC to afford the desired product as a white solid (12 mg).

APCI-MS (M+H$^+$)=612

EXAMPLE 13

Determination of IC$_{50}$

The compounds of the present invention are first dissolved in a buffer to give solutions containing concentrations such that assay concentrations range from 0–100 µM. In assays for thrombin, prothrombinase and factor Xa, a synthetic chromogenic substrate would be added to a solution containing a test compound and the enzyme of interest and the residual catalytic activity of that enzyme would then be determined spectrophotometrically.

The IC$_{50}$ of a compound is determined from the substrate turnover. The IC$_{50}$ is the concentration of test compound giving 50% inhibition of the substrate turnover. Preferred compounds of the invention desirably have an IC$_{50}$, of less than 500 nM in the factor Xa assay, preferably less than 200 nM, and more preferably less than 100 nM. Preferred compounds of the invention desirably have an IC$_{50}$ of less than 4.0 µM in the prothrombinase assay, preferably less than 200 nM, and more preferably less than 10 nM. Preferred compounds of the invention desirably have an IC$_{50}$ of greater than 1.0 µM in the thrombin assay, preferably greater than 10.0 µM, and more preferably greater than 100.0 µM.

Amidolytic Assays for Determining Protease Inhibition Activity

Factor Xa and thrombin assays are performed at room temperature, in 0.02 M Tris HCl buffer, pH 7.5, containing 0.15 M NaCl. The rates of hydrolysis of the paranitroanilide substrate S-2765 (Chromogenix) for factor Xa, and the substrate Chromozym TH (Boehringer Mannheim) for thrombin following preincubation of the enzyme with the test compound for 5 minutes at room temperature are determined using a Softmax 96-well plate reader (Molecular Devices), monitored at 405 nm to measure the time dependent appearance of p-nitroanilide.

The prothrombinase inhibition assay is performed in a plasma free system with modifications to the method as described by Sinha, et al., *Thromb. Res.*, 75:427–436 (1994). The activity of the prothrombinase complex is determined by measuring the time course of thrombin generation using the p-nitroanilide substrate Chromozym TH. The assay consists of a 5 minute preincubation of selected compounds to be tested as inhibitors with the complex formed from factor Xa (0.5 nM), factor Va (2 nM), phosphatidyl serine-:phosphatidyl choline (25:75, 20 µM) in 20 mM Tris HCl buffer, pH 7.5, containing 0.15 M NaCl, 5 mM CaCl$_2$ and 0.1% bovine serum albumin. Aliquots from the complex-test compound mixture are added to prothrombin (1 nM) and Chromozym TH (0.1 mM). The rate of substrate cleavage is monitored at 405 nm for two minutes. Several concentrations of a given test compound are assayed in duplicate. A standard curve of thrombin generation by an equivalent amount of untreated complex is then used for determination of percent inhibition.

The compounds of the invention exhibited inhibitory activity in the Factor Xa assay described above. The preferred compounds of the invention have IC$_{50}$ values less than 100 nM.

EXAMPLE 14

The antithrombotic efficacy of the compounds of this invention can readily be evaluated using a series of studies in rabbits, as described below. These studies are also useful in evaluating a compounds effects on hemostasis and its the hematological parameters.

Antithrombotic Efficacy in a Rabbit Model of Venous Thrombosis

A rabbit deep vein thrombosis model as described by Hollenbach, et al., *Thromb. Haemost.* 71:357–362 (1994), is used to determine the in vivo antithrombotic activity of the compounds of the present invention. Rabbits are anesthetized with I.M. injections of Ketamine, Xylazine, and Acepromazine cocktail.

A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is then used as a measure of the antithrombotic activity of the compound being evaluated. Test agents or control saline are administered through a marginal ear vein catheter. A femoral vein catheter is used for blood sampling prior to and during steady state infusion of the compound being evaluated. Initiation of thrombus formation will begin immediately after advancement of the cotton thread apparatus into the central venous circulation. The compounds being evaluated are administered from time=30 minutes to time=150 minutes at which point the experiment is terminated. The rabbits are euthanized and the thrombus excised by surgical dissection and characterized by weight and histology. Blood samples are then analyzed for changes in hematological and coagulation parameters.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A compound having the formula:

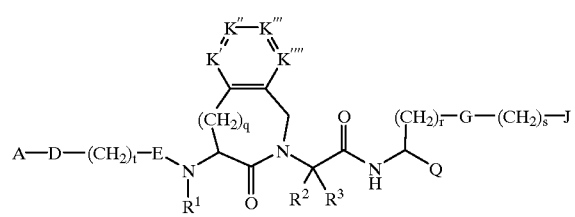

(I)

Wherein:

R$^1$ and R$^2$ are independently selected from the group consisting of H, C$_{1-6}$alkyl, C$_{3-8}$cycloalkyl, C$_{1-3}$alkylaryl, C$_{1-3}$alkyl-C$_{3-8}$cycloalkyl and aryl;

R$^3$ is H, C$_{1-6}$alkyl, or R$^2$ and R$^3$ are taken together to form a carbocyclic ring;

q is an integer equal to 1;

r is an integer from 0–4;

s is an integer from 0–1;

t is an integer from 0–4;

A is selected from the group consisting of $R^8$, —$NR^8R^9$,

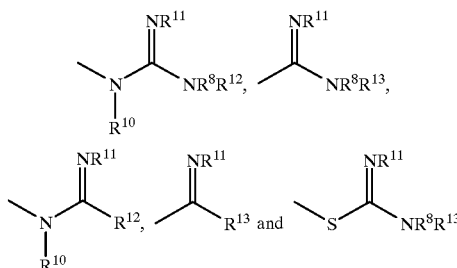

where $R^8$, $R^9$, $R^{10}$ and $R^{11}$ are independently selected from the group consisting of H, —OH, $C_{1-6}$alkyl, aryl and $C_{1-4}$alkylawyl; $R^{12}$ is selected from the group consisting of H, $C_{1-6}$alkyl, aryl and $C_{1-4}$alkylaryl, or can be taken together with $R^{10}$ or $R^{11}$ to form a 5–6 membered ring; and $R^{13}$ is selected from the group consisting of H, $C_{1-6}$alkyl, aryl and $C_{1-4}$alkylaryl, or can be taken together with $R^{11}$ to form a 5–6 membered ring;

D is selected from the group consisting of a direct link, $C_{3-8}$cycloalkyl, $C_{1-6}$alkenyl, $C_{1-6}$alkenylaryl, aryl and a five to ten membered heterocyclic ring system containing 1–4 heteroatoms selected from the group consisting of N, O and S;

E is selected from the group consisting of a direct link, —CO—, —$SO_2$—, —O—CO—, —$NR^{14}$—$SO_2$— and —$NR^{14}$—CO—, where $R^{14}$ is selected from the group consisting of H, —OH, $C_{1-6}$alkyl, aryl and $C_{1-4}$alkylaryl;

G is selected from the group consisting of a direct link, $C_{3-8}$cycloalkyl, aryl, and a five to ten membered heterocyclic ring system containing 1–4 heteroatoms selected from the group consisting of N, O and S;

J is selected from the group consisting of $R^{15}$, —$NR^{15}R^{16}$,

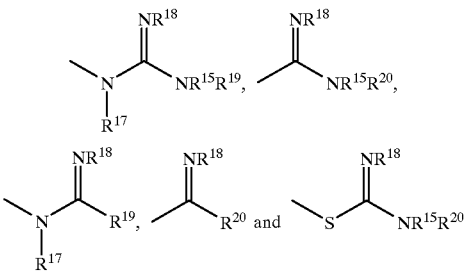

where $R^{15}$, $R^{16}$, $R^{17}$ and $R^{18}$ are independently selected from the group consisting of H, —OH, $C_{1-6}$alkyl, aryl and $C_{1-4}$alkylaryl; $R^{19}$ is selected from the group consisting of H, $C_{1-6}$alkyl, aryl and $C_{1-4}$alkylaryl, or can be taken together with $R^{17}$ or $R^{18}$ to form a 5–6 membered ring; and $R^{20}$ is selected from the group consisting of H, $C_{1-6}$alkyl, aryl and $C_{1-4}$alkylaryl, or can be taken together with $R^{18}$ to form a 5–6 membered ring; with the proviso that when J is $R^{15}$, then G must contain at least one N atom;

K', K", K'" and K"" are each —CH—;

Q is selected from the group consisting of H,

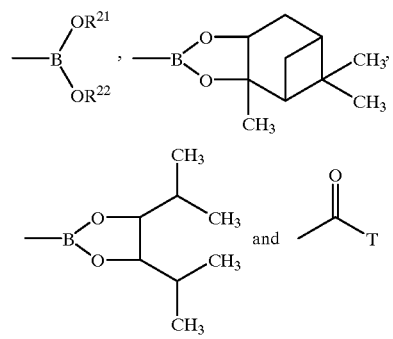

where $R^{21}$ and $R^{22}$ are independently selected from the group consisting of H, $C_{1-3}$alkyl and aryl; and T is selected from the group consisting of H, —$COOR^{23}$, —$CONR^{23}R^{24}$, —$CF_3$, —$CF_2CF_3$ and a group having the formula:

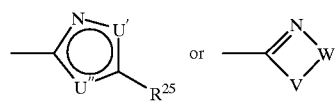

where: $R^{23}$ and $R^{24}$ are independently selected from the group consisting of H, $C_{1-6}$alkyl, aryl and $C_{1-4}$alkylaryl; U' and U" are independently selected from the group consisting of —O—, —S—, —N— and —NH—; with the proviso that at least one of U' or U" is —N— or —NH—; $R^{25}$ is selected from the group consisting of H, $C_{1-4}$alkyl, $C_{2-6}$alkenyl, $C_{0-6}$alkylaryl, $C_{2-6}$alkenylaryl, $C_{0-6}$alkylheterocyclo, $C_{2-6}$alkenylheterocyclo, —$CF_3$ and —$CF_2CF_3$; V is selected from the group consisting of —S—, —SO—, —$SO_2$—, —O— and —$NR^{26}$—, where $R^{26}$ is selected from the group consisting of H, $C_{1-6}$alkyl and benzyl; and W is selected from the group consisting of:

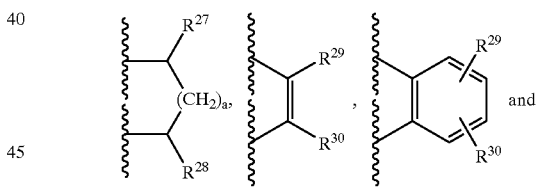

a $C_{6-10}$ heterocyclic ring system substituted by $R^{29}$ and $R^{30}$ and containing 1–4 heteroatoms selected from N, S and O; where: a is an integer from 0–2; $R^{27}$ and $R^{28}$ are independently selected from the group consisting of H, $C_{1-6}$alkyl, aryl, $C_{1-6}$alkylaryl, —$COOR^{31}$, —$CONR^{31}R^{32}$, —CN and —$CF_3$; and $R^{29}$ and $R^{30}$ are independently selected from the group consisting of H, $C_{1-6}$alkyl, aryl, $C_{1-6}$alkylaryl, $C_{1-4}$alkyloxy, halogen, —$NO_2$, —$NR^{31}R^{32}$, —$NR^{31}COR^{32}$, —$OR^{31}$, —$OCOR^{31}$, —$COOR^{31}$, —$CONR^{31}R^{32}$, —CN, —$CF_3$, —$SO_2NR^{31}R^{32}$ and $C_{1-6}$alkyl—$OR^{31}$; where $R^{31}$ and $R^{32}$ are independently selected from the group consisting of H, $C_{1-6}$alkyl, $C_{1-3}$alkylaryl and aryl; or all pharmaceutically acceptable salts or optical isomers thereof.

2. The compound of claim 1 wherein $R^1$ is selected from the group consisting of H and $C_{1-6}$alkyl.

3. The compound of claim 2 wherein $R^1$ is selected from the group consisting of H and methyl.

4. The compound of claim 3 wherein $R^1$ is H.

5. The compound of claim 1 wherein $R^2$ is selected from the group consisting of H and $C_{1-6}$alkyl.

6. The compound of claim 5 wherein $R^2$ is selected from the group consisting of H and methyl.

7. The compound of claim 6 wherein $R^3$ is H.

8. The compound of claim 1 wherein $R^3$ is H.

9. The compound of claim 1 wherein the integer "r" is 3.

10. The compound of claim 1 wherein the integer "s" is 0.

11. The compound of claim 1 wherein the integer "t" is from 0–1.

12. The compound of claim 1 wherein $R^8$, $R^9$, $R^{10}$ and $R^{11}$ are independently selected from the group consisting of H and $C_{1-6}$alkyl.

13. The compound of claim 12 wherein $R^8$, $R^9$, $R^{10}$ and $R^{11}$ are independently selected from the group consisting of H and methyl.

14. The compound of claim 1 wherein $R^{12}$ is H, $C_{1-6}$alkyl or taken together with $R^{10}$ or $R^{11}$ to form a 5–6 membered ring.

15. The compound of claim 14 wherein $R^{12}$ is H or methyl.

16. The compound of claim 1 wherein $R^{13}$ is H, $C_{1-6}$alkyl or taken together with $R^{10}$ to form a 5–6 membered ring.

17. The compound of claim 16 wherein $R^{13}$ is H or methyl.

18. The compound of claim 1 wherein D is selected from the group consisting of a direct link, $C_{3-8}$cycloalkyl, aryl and a five to ten membered heterocyclic ring system containing 1–4 heteroatoms selected from the group consisting of N, O and S.

19. The compound of claim 1 wherein E is a direct link, —CO— or —SO$_2$—.

20. The compound of claim 1 wherein G is a direct link.

21. The compound of claim 1 wherein $R^{15}$, $R^{16}$, $R^{17}$, $R^{18}$, $R^{19}$ and $R^{20}$ are independently selected from the group consisting of H and $C_{1-6}$alkyl.

22. The compound of claim 21 wherein $R^{15}$, $R^{16}$, $R^{17}$, $R^{18}$, $R^{19}$ and $R^{20}$ are independently selected from the group consisting of H and methyl.

23. The compound of claim 1 wherein Q is:

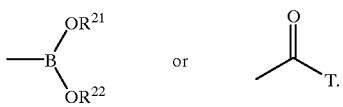

24. The compound of claim 23 wherein $R^{21}$ is H.

25. The compound of claim 24 wherein $R^{22}$ is H.

26. The compound of claim 23 wherein T is H, —COOR$^{23}$, —CONR$^{23}$R$^{24}$ or a group having the formula:

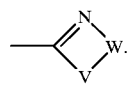

27. The compound of claim 26 wherein $R^{23}$ is H.

28. The compound of claim 26 wherein $R^{24}$ is $C_{1-4}$alkylaryl.

29. The compound of claim 26 wherein V is —S—, —O— or —NR$^{26}$—.

30. The compound of claim 29 wherein $R^{26}$ is H or methyl.

31. The compound of claim 30 wherein $R^{26}$ is H.

32. The compound of claim 26 wherein W is selected from the group consisting of:

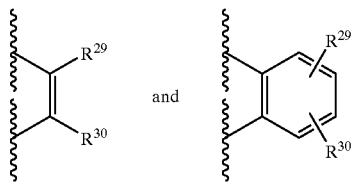

33. The compound of claim 32 wherein W is:

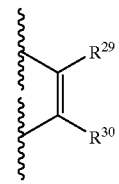

34. The compound of claim 32 wherein $R^{29}$ and $R^{30}$ are independently selected from the group consisting of H, —O—R$^{31}$, —COOR$^{31}$, —CONR$^{31}$R$^{32}$ or —CF$_3$.

35. The compound of claim 34 wherein $R^{29}$ is H.

36. The compound of claim 34 wherein $R^{30}$ is H.

37. The compound of claim 1 wherein W is:

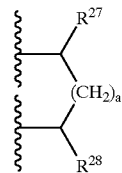

and $R^{27}$ is H.

38. The compound of claim 37 wherein $R^{28}$ is H.

39. The compound of claim 33 wherein T is:

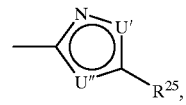

U' is O, U" is N and $R^{25}$ is —CF$_3$ or —CF$_2$CF$_3$.

40. A compound having the formula:

(II)

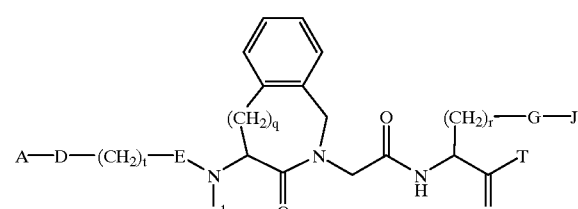

Wherein:
R$^1$ is selected from the group consisting of H, $C_{1-6}$alkyl, $C_{3-8}$cycloalkyl, $C_{1-3}$alkylaryl, $C_{1-3}$alkyl—$C_{3-8}$cycloalkyl and aryl;
q is an integer equal to 1;
r is an integer from 0–4;
t is an integer from 0–4;

43

A is selected from the group consisting of $R^8$, —$NR^8R^9$,

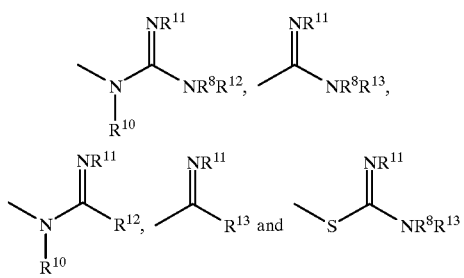

where $R^8$, $R^9$, $R^{10}$ and $R^{11}$ are independently selected from the group consisting of H, —OH, $C_{1-6}$alkyl, aryl and $C_{1-4}$alkylaryl; $R^{12}$ is selected from the group consisting of H, $C_{1-6}$alkyl, aryl and $C_{1-4}$alkylaryl, or can be taken together with $R^{10}$ or $R^{11}$ to form a 5–6 membered ring; and $R^{13}$ is selected from the group consisting of H, $C_{1-6}$alkyl, aryl and $C_{1-4}$alkylaryl, or can be taken together with $R^{11}$ to form a 5–6 membered ring;

D is selected from the group consisting of a direct link, $C_{3-8}$cycloalkyl, $C_{1-6}$alkenyl, $C_{1-6}$alkenylaryl, aryl and a five to ten membered heterocyclic ring system containing 1–4 heteroatoms selected from the group consisting of N, O and S;

E is selected from the group consisting of a direct link, —CO—, —$SO_2$—, —O—CO—, —$NR^{14}$—$SO_2$— and —$NR^{14}$—CO—, where $R^{14}$ is selected from the group consisting of H, —OH, $C_{1-6}$alkyl, aryl and $C_{1-4}$alkylaryl;

G is selected from the group consisting of a direct link, $C_{3-8}$cycloalkyl, aryl, and a five to ten membered heterocyclic ring system containing 1–4 heteroatoms selected from the group consisting of N, O and S;

J is selected from the group consisting of $R^{15}$, —$NR^{15}R^{16}$,

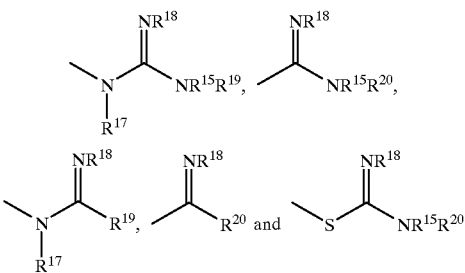

where $R^{15}$, $R^{16}$, $R^{17}$ and $R^{18}$ are independently selected from the group consisting of H, —OH, $C_{1-6}$alkyl, aryl and $C_{1-4}$alkylaryl; $R^{19}$ is selected from the group consisting of H, $C_{1-6}$alkyl, aryl and $C_{1-4}$alkylaryl, or can be taken together with $R^{17}$ or $R^{18}$ form a 5–6 membered ring; and $R^{20}$ is selected from the group consisting of H, $C_{1-6}$alkyl, aryl and $C_{1-4}$alkylaryl, or can be taken together with $R^{18}$ to form a 5–6 membered ring; with the proviso that when J is $R^{15}$, then G must contain at least one N atom;

T is selected from the group consisting of H, —$COOR^{23}$, —$CONR^{23}R^{24}$, —$CF_3$, —$CF_2CF_3$ and a group having the formula:

44

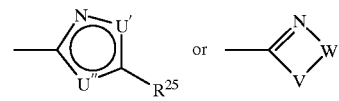

where: $R^{23}$ and $R^{24}$ are independently selected from the group consisting of H, $C_{1-6}$alkyl, aryl and $C_{1-4}$alkylaryl; U' and U" are independently selected from the group consisting of —O—, —S—, —N— and —NH—; with the proviso that at least one of U' or U" is —N— or —NH—; $R^{25}$ is selected from the group consisting of H, $C_{1-6}$alkyl, $C_{2-6}$akenyl, $C_{0-6}$alkylaryl, $C_{2-6}$alkenylaryl, $C_{0-6}$alkylheterocyclo, $C_{2-6}$alkenylheterocyclo, —$CF_3$ and —$CF_2CF_3$; V is selected from the group consisting of —S—, —SO—, —$SO_2$—, —O— and —$NR^{26}$—, where $R^{26}$ is selected from the group consisting of H, $C_{1-6}$alkyl and benzyl; and W is selected from the group consisting of:

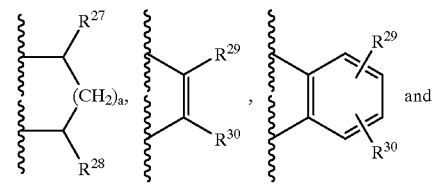

a $C_{6-10}$ heterocyclic ring system substituted by $R^{29}$ and $R^{30}$ and containing 1–4 heteroatoms selected from N, S and O; where: a is an integer from 0–2; $R^{27}$ and $R^{28}$ are independently selected from the group consisting of H, $C_{1-6}$alkyl, aryl, $C_{1-6}$alkylaryl, —$COOR^{31}$, —$CONR^{31}R^{32}$, —CN and —$CF_3$; and $R^{29}$ and $R^{30}$ are independently selected from the group consisting of H, $C_{1-6}$alkyl, aryl, $C_{1-6}$alkylaryl, $C_{1-4}$alkyloxy, halogen, —$NO_2$, —$NR^{31}R^{32}$, —$NR^{31}COR^{32}$, —$OR^{31}$, —$OCOR^{31}$, —$COOR^{31}$, —$CONR^{31}R^{32}$, —CN, —$CF_3$, —$SO_2NR^{31}R^{32}$ and $C_{1-6}$alkyl—$OR^{31}$; where $R^{31}$ and $R^{32}$ are independently selected from the group consisting of H, $C_{1-6}$alkyl, $C_{1-3}$alkylaryl and aryl; or all pharmaceutically acceptable salts or optical isomers thereof.

41. A compound having the formula:

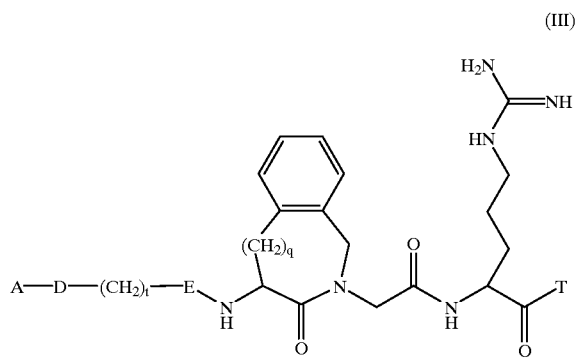

(III)

Wherein:

q is an integer equal to 1;

t is an integer from 0–4;

A is selected from the group consisting of $R^8$, —$NR^8R^9$,

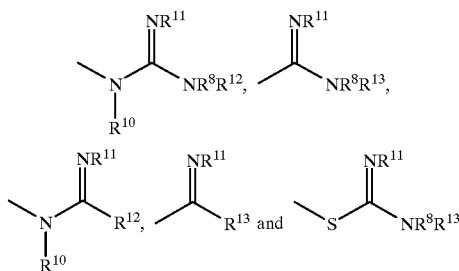

where $R^8$, $R^9$, $R^{10}$ and $R^{11}$ are independently selected from the group consisting of H, —OH, $C_{1-6}$alkyl, aryl and $C_{1-4}$alkylaryl; $R^{12}$ is selected from the group consisting of H, $C_{1-6}$alkyl, aryl and $C_{1-4}$alkylaryl, or can be taken together with $R^{10}$ or $R^{11}$ to form a 5–6 membered ring; and $R^{13}$ is selected from the group consisting of H, $C_{1-6}$alkyl, aryl and $C_{1-4}$alkylaryl, or can be taken together with $R^{11}$ to form a 5–6 membered ring;

D is selected from the group consisting of a direct link, $C_{3-8}$cycloalkyl, $C_{1-6}$alkenyl, $C_{1-6}$alkenylaryl, aryl and a five to ten membered heterocyclic ring system containing 1–4 heteroatoms selected from the group consisting of N, O and S;

E is selected from the group consisting of a direct link, —CO—, —$SO_2$—, —O—CO—, —$NR^{14}$—$SO_2$— and —$NR^{14}$—CO—, where $R^{14}$ is selected from the group consisting of H, —OH, $C_{1-6}$alkyl, aryl and $C_{1-4}$alkylaryl;

T is selected from the group consisting of H, —$COOR^{23}$, —$CONR^{23}R^{24}$, —$CF_3$, —$CF_2CF_3$ and a group having the formula:

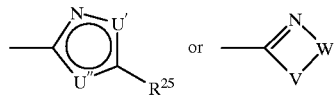

where: $R^{23}$ and $R^{24}$ are independently selected from the group consisting of H, $C_{1-6}$alkyl, aryl and $C_{1-4}$alkylaryl; U' and U" are independently selected from the group consisting of —O—, —S—, —N— and —NH—; with the proviso that at least one of U' or U" is —N— or —NH—; $R^{25}$ is selected from the group consisting of H, $C_{1-6}$alkyl, $C_{2-6}$alkenyl, $C_{0-6}$alkylaryl, $C_{2-6}$alkenylaryl, $C_{0-6}$aylheterocyclo, $C_{2-6}$alkenylheterocyclo, —$CF_3$ and —$CF_2CF_3$; V is selected from the group consisting of —S—, —SO—, —$SO_2$—, —O— and —$NR^{26}$—, where $R^{26}$ is selected from the group consisting of H, $C_{1-6}$alkyl and benzyl; and W is selected from the group consisting of:

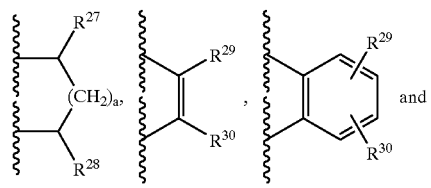

a $C_{6-10}$ heterocyclic ring system substituted by $R^{29}$ and $R^{30}$ and containing 1–4 heteroatoms selected from N, S and O; where: a is an integer from 0–2; $R^{27}$ and $R^{28}$ are independently selected from the group consisting of H, $C_{1-6}$alkyl, aryl, $C_{1-6}$alkylaryl, —$COOR^{31}$, —$CONR^{31}R^{32}$, —CN and —$CF_3$; and $R^{29}$ and $R^{30}$ are independently selected from the group consisting of H, $C_{1-6}$alkyl, aryl, $C_{1-6}$alkylaryl, $C_{1-4}$alkyloxy, halogen, —$NO_2$, —$NR^{31}R^{32}$, —$NR^{31}COR^{32}$, —$OR^{31}$, —$OCOR^{31}$, —$COOR^{31}$, —$CONR^{31}R^{32}$, —CN, —$CF_3$, —$SO_2NR^{31}R^{32}$ and $C_{1-6}$alkyl—$OR^{31}$; where $R^{31}$ and $R^{32}$ are independently selected from the group consisting of H, $C_{1-6}$alkyl, $C_{1-3}$alkylaryl and aryl; or all pharmaceutically acceptable salts or optical isomers thereof.

42. A pharmaceutical composition for preventing or treating a condition in a mammal characterized by undesired thrombosis comprising a pharmaceutically acceptable carrier and the compound of claim 1.

43. A method for preventing or treating a condition in a mammal characterized by undesired thrombosis comprising administering to said mammal a therapeutically effective amount of the compound of claim 1.

44. The method of claim 43, wherein the condition is selected from the group consisting of: the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries, deep venous thrombosis, pulmonary embolism, myocardial infarction, stroke, thromboembolic complications of surgery and peripheral arterial occlusion, occlusive coronary thrombus formation resulting from either thrombolytic therapy or percutaneous transluminal coronary angioplasty, thrombus formation in the venous vasculature and disseminated intravascular coagulopathy.

45. A method for inhibiting the coagulation of biological samples, comprising the administration of the compound of claim 1.

* * * * *